US011827887B2

(12) United States Patent
Abo et al.

(10) Patent No.: US 11,827,887 B2
(45) Date of Patent: Nov. 28, 2023

(54) ALKALINE PHOSPHATASE FUSION ANTIBODY AND METHOD FOR PRODUCING THE SAME, AND IMMUNOASSAY METHOD

(71) Applicant: SYSMEX CORPORATION, Kobe (JP)

(72) Inventors: Hirotaka Abo, Kobe (JP); Nobuyuki Ide, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 145 days.

(21) Appl. No.: 17/332,208

(22) Filed: May 27, 2021

(65) Prior Publication Data

US 2021/0371867 A1    Dec. 2, 2021

(30) Foreign Application Priority Data

May 28, 2020 (JP) ................. 2020-093429

(51) Int. Cl.
| | |
|---|---|
| C12N 15/62 | (2006.01) |
| C07K 14/195 | (2006.01) |
| C07K 14/47 | (2006.01) |
| C07K 16/46 | (2006.01) |
| C12N 9/16 | (2006.01) |
| G01N 33/543 | (2006.01) |

(52) U.S. Cl.
CPC ............ *C12N 15/62* (2013.01); *C07K 14/195* (2013.01); *C07K 14/47* (2013.01); *C07K 16/46* (2013.01); *C12N 9/16* (2013.01); *G01N 33/54306* (2013.01)

(58) Field of Classification Search
None
See application file for complete search history.

(56) References Cited

U.S. PATENT DOCUMENTS

| | | | |
|---|---|---|---|
| 6,406,899 B1 | 6/2002 | Hoelke et al. | |
| 2018/0230445 A1 | 8/2018 | Jaluria et al. | |

FOREIGN PATENT DOCUMENTS

| | | |
|---|---|---|
| JP | 08-070875 A | 3/1996 |
| JP | H11-332586 A | 12/1999 |
| JP | 2001-183375 A | 7/2001 |
| JP | 3657895 B2 | 6/2005 |
| JP | 6080040 B2 | 2/2017 |
| JP | 2020-509744 A | 4/2020 |
| WO | 93/18139 A1 | 9/1993 |
| WO | 2012/115023 A1 | 8/2012 |
| WO | 2017/214130 A1 | 12/2017 |
| WO | 2018/164995 A1 | 9/2018 |

OTHER PUBLICATIONS

Liu et al., "Development of a Nanobody- Alkaline Phosphatase fusion protein and its application in a highly sensitive direct competitive fluorescene enzyme immunoassay for detection of Ochratoxin A in Cereal", (Anal. Chem. 87: 1387-1394 (Year: 2015).*
Aiba et al., "Over-expression, characterization, and modification of highly active alkaline phosphatase from a *Shewanella* genus bacterium", (Bioscience, Biotechnology, and Biochemistry vol. 81, No. 10, pp. 1994-2001 (Year: 2017).*
Marco Chapter 32, Dirk Saerens and Serge Muyldermans (eds.), Single Domain Antibodies: Methods and Protocols, Methods in Molecular Biology, vol. 911, DOI: 10.1007/978-1-61779-968-6_32 (Year: 2012).*
PDF copy of Abnova Alkaline Phosphatase labeling kit (Catalog No. KA0001) instructions downloaded (Year: 2023).*
Extended European search report dated Jan. 24, 2022 in a counterpart European patent application No. 21176405.5.
Thomas Manes et al., "Genetic Complexity, Structure, and Characterization of Highly Active Bovine Intestinal Alkaline Phosphatases", The Journal of Biological Chemistry, Sep. 4, 1998, pp. 23353-23360, vol. 273, No. 36, The American Society for Biochemistry and Molecular Biology, Inc., U.S.A.
Yoshiyuki Sasajima et al., "Expression of antibody variable region-human alkaline phosphatase fusion proteins in mammalian cells", Journal of Immunological Methods, Aug. 2010, pp. 57-63, vol. 361, Elsevier B.V.
Etienne Weiss et al., "Application of an alkaline phosphatase fusion protein system suitable for efficient screening and production of Fab-enzyme conjugates in *Escherichia coli*", Journal of Biotechnology, 1994, pp. 43-53, vol. 33, Elsevier Science B.V.
Helge Weissig et al: "Cloning and expression of the bovine intestinal alkaline phosphatase gene: biochemical characterization of the recombinant enzyme", Biochemical Journal, 1993, vol. 290, pp. 503-508.
Hiroshi Aiba et al: "Over-expression, characterization, and modification of highly active alkaline phosphatase from a *Shewanella* genus bacterium", Bioscience, Biotechnology, and Biochemistry, 2017, vol. 81, No. 10, pp. 1994-2001, Japan Society for Bioscience, Biotechnology, and Agrochemistry.
Marc Besman et al: "Isozymes of Bovine Intestinal Alkaline Phosphatase", The Journal of Biological Chemistry, Sep. 15, 1985, vol. 260, No. 20, pp. 11190-11193, The American Society of Biological Chemists, Inc.
Partial European search report dated Oct. 20, 2021 in a counterpart European patent application No. 21176405.5.
Japanese Office Action dated Sep. 26, 2023 in a counterpart Japanese patent application No. 2020-093429.

\* cited by examiner

*Primary Examiner* — Anand U Desai
(74) *Attorney, Agent, or Firm* — Sughrue Mion, PLLC

(57) ABSTRACT

Disclosed is a method for producing an alkaline phosphatase fusion antibody, comprising: culturing a cell comprising an expression vector comprising a gene encoding alkaline phosphatase derived from bovine small intestine or *Shewanella* bacterium and a gene encoding an antibody in a medium comprising a zinc ion, and acquiring an alkaline phosphatase fusion antibody expressed by the cell.

18 Claims, 22 Drawing Sheets
Specification includes a Sequence Listing.

ANTIBODY EXAMPLE 1-1

ANTIBODY EXAMPLE 2-1

ANTIBODY EXAMPLE 1-2

ANTIBODY EXAMPLE 2-2

ANTIBODY EXAMPLE 1-3

ANTIBODY EXAMPLE 2-3

ANTIBODY EXAMPLE 1-4

ANTIBODY EXAMPLE 2-4

ANTIBODY EXAMPLE 4-1

ANTIBODY EXAMPLE 5-1

ANTIBODY EXAMPLE 4-2

ANTIBODY EXAMPLE 5-2

ANTIBODY EXAMPLE 4-3

ANTIBODY EXAMPLE 5-3

ANTIBODY EXAMPLE 4-4

ANTIBODY EXAMPLE 5-4

ALKALINE PHOSPHATASE FUSION ANTIBODY AND METHOD FOR PRODUCING THE SAME, AND IMMUNOASSAY METHOD

CROSS REFERENCE TO RELATED APPLICATIONS

This application claims priority from prior Japanese Patent Application No. 2020-093429, filed on May 28, 2020, entitled "Alkaline phosphatase fusion antibody and method for producing the same, and immunoassay reagent and immunoassay method", the entire contents of which are incorporated herein by reference.

FIELD OF THE INVENTION

The present invention relates to an alkaline phosphatase fusion antibody and a method for producing the same. The present invention relates to an immunoassay method using an alkaline phosphatase fusion antibody.

BACKGROUND

Alkaline phosphatase (ALP) is an enzyme that hydrolyzes a phosphate monoester bond to produce inorganic phosphate, and is often used to label an antibody in immunoassay such as enzyme immunoassay (EIA). Labeling of an antibody with ALP is conventionally performed by chemical modification method in which ALP and an antibody are chemically bonded using a crosslinking agent or the like. For example, Japanese Laid-Open Patent Publication No. 2001-183375 describes that ALP and an antibody were bound using a crosslinking agent and purified by a plurality of column chromatography to obtain a homogeneous ALP-labeled antibody.

It is difficult to control a binding position between ALP and an antibody and the number of antibodies that bind to ALP in the chemical modification method. Therefore, the ALP-labeled antibody obtained by the chemical modification method is heterogeneous. Use of such a heterogeneous ALP-labeled antibody in immunoassay affects measurement accuracy. In order to obtain a homogeneous ALP-labeled antibody by the chemical modification method, purification is required a plurality of times as described in Japanese Laid-Open Patent Publication No. 2001-183375, which is complicated.

An object of the present invention is to provide an ALP fusion antibody and a method for producing the same, and an immunoassay reagent and an immunoassay method.

SUMMARY OF THE INVENTION

The scope of the present invention is defined solely by the appended claims, and is not affected to any degree by the statements within this summary.

The present inventors have found that an ALP fusion antibody using ALP derived from bovine small intestine or *Shewanella* bacterium is suitable for immunoassay such as EIA, and completed the present invention.

The present invention provides a method for producing an ALP fusion antibody, including culturing a cell containing an expression vector containing a gene encoding ALP derived from bovine small intestine or *Shewanella* bacterium and a gene encoding an antibody in a medium containing a zinc ion, and acquiring an ALP fusion antibody expressed by the cell.

The present invention provides an ALP fusion antibody in which an ALP derived from bovine small intestine or *Shewanella* bacterium and an antibody are bound directly or via a peptide linker.

The present invention provides a method for assaying a test substance, comprising: forming a complex on a solid phase, wherein the complex comprises: a capture substance that specifically binds to the test substance and immobilized on the solid phase; the test substance; and a detection antibody that specifically binds to the test substance, and wherein the detection antibody is an alkaline phosphatase fusion antibody in which alkaline phosphatase derived from bovine small intestine or *Shewanella* bacterium and an antibody are bound directly or via a peptide linker; reacting the complex on the solid phase with a substrate of the alkaline phosphatase; and detecting a signal generated in the reacting to detect the test substance.

DETAILED DESCRIPTION OF THE PREFERRED EMBODIMENTS

Figure 1A:
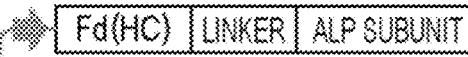
FIG. 1A shows schematic diagrams of constitution examples of expression vectors.
Figure 1A:
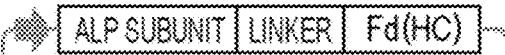
Figure 1A:
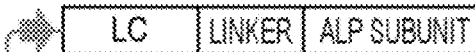
Figure 1A:
Figure 1A:
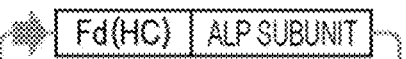
Figure 1A:
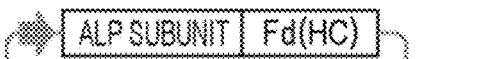
Figure 1A:
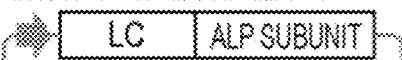
Figure 1A:
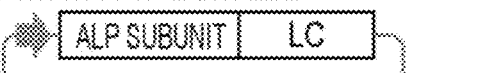

In the method for producing an ALP fusion antibody of the present embodiment (hereinafter, also referred to as "production method"), a cell containing an expression vector containing a gene encoding ALP derived from bovine small intestine or *Shewanella* bacterium and a gene encoding an antibody is cultured in a medium containing a zinc ion.

In the production method of the present embodiment, a polypeptide in which ALP and an antibody are bound directly or by a peptide bond via a peptide linker, that is, a polypeptide in which ALP and an antibody are integrated at an amino acid level is acquired. On the other hand, in the chemical modification method, an antibody and ALP are acquired separately, and these proteins are bonded by a crosslinking agent to acquire an ALP-labeled antibody in which ALP is linked to the antibody via the crosslinking agent.

In the present embodiment, the types of bovine small intestine-derived ALP (BIAP) and *Shewanella* bacterium-derived ALP (S-AP) are not particularly limited, and can be appropriately selected from known BIAP and S-AP. Since an ALP fusion antibody is produced by gene recombination in the production method of the present embodiment, it is preferable that an amino acid sequence of BIAP and S-AP or a base sequence encoding the same are determined. The amino acid sequence or base sequence of BIAP and S-AP may be acquired from a known database. Examples of the database include GenBank and the like.

Examples of BIAP include BIAP I, BIAP II, BIAP III, BIAP IV, BIAP V, BIAP VI, BIAP VII, and the like (see Manes T. et al., (1998) J. Biol. Chem., Vol. 273, pp. 23353-23360, U.S. Pat. No. 6,406,899, etc.). Among them, BIAP II is particularly preferable. An amino acid sequence of BIAPII and a base sequence encoding the same are shown in SEQ ID NOs: 1 and 2, respectively. Manes T. et al., (1998) J. Biol. Chem., vol. 273, pp. 23353-23360 and U.S. Pat. No. 6,406,899 are incorporated herein by reference.

Examples of S-AP include ALP derived from bacteria selected from *Shewanella* sp. T3-3 (see U.S. Pat. No. 9,133,446), *Shewanella putrefaciens* CN-32, *Shewanella xiamenensis*, *Shewanella oneidensis*, *Shewanella frigidimarina*, *Shewanella arctica* sp., *Shewanella frigidimarina* NCIMB400, *Shewanella livingstonensis*, *Shewanella* sp. R106 (or M2), *Shewanella* sp. ALD9, *Shewanella colwelliana*, *Shewanella* sp. CG18, *Shewanella vesiculosa*, *Shewanella benthica* KT99, *Shewanella benthica*, and *Shewanella algidipiscicola*. Amino acid sequences themselves of ALPs derived from these bacteria are known, and can be acquired from known databases such as database provided by NCBI (National Center for Biotechnology Information). Amino acid sequences of ALPs derived from *Shewanella* bacteria other than *Shewanella* sp. T3-3 are registered in the NCBI database with accession numbers shown in Reference Examples described later. U.S. Pat. No. 9,133,446 is incorporated herein by reference.

In the present embodiment, ALP derived from bacteria selected from *Shewanella* sp. T3-3, *Shewanella putrefaciens* CN-32, *Shewanella xiamenensis*, *Shewanella frigidimarina*, *Shewanella livingstonensis* and *Shewanella* vesiculosa is preferable. An amino acid sequence of S-AP derived from *Shewanella* sp. T3-3 and a base sequence encoding the same are shown in SEQ ID NOs: 3 and 4, respectively.

In the present embodiment, a gene encoding BIAP or S-AP (hereinafter, also referred to as "ALP gene") may be cloned from a genomic DNA of bovine small intestine or *Shewanella* bacterium by a conventional method, or may be synthesized based on a known amino acid sequence or base sequence.

As used herein, the term "antibody" includes full-length antibodies and fragments thereof. The full-length antibody may be IgG, IgA, IgM, IgD or IgE, and is preferably IgG. Examples of the antibody fragments include Fab, Fab', F(ab')2, Fd, Fd', Fv, light chain, heavy chain variable region (VHH) of heavy chain antibody, reduced IgG (rIgG), one chain antibodies (scFv), and the like.

In the present embodiment, the antibody is not particularly limited, and may be an antibody recognizing any antigen. The antibody may be an antibody having a natural amino acid sequence (wild-type antibody) or an artificially produced antibody. The artificially produced antibody refers to an antibody in which the amino acid sequence is artificially altered. Examples of such an antibody include antibodies in which an amino acid sequence of complementarity determining region (CDR) is altered, chimeric antibodies, humanized antibodies, bispecific antibodies, and the like. The antibody may be an antibody derived from any animal. Such animals are preferably mammals, and examples thereof include rabbits, mice, alpacas, camels, rats, pigs, sheep, goats, cows, horses, humans, and the like.

In the present embodiment, it is preferable that the antibody has an amino acid sequence or a base sequence encoding the same. Examples of such an antibody include an antibody in which the amino acid sequence of the antibody or a base sequence encoding the antibody is disclosed in a known database, an antibody for which a hybridoma that produces the antibody is available, and the like. Examples of the database include GenBank, abYsis, IMGT, and the like. The gene encoding the antibody (hereinafter, also referred to as "antibody gene") may be synthesized based on a known amino acid sequence or base sequence. When there is a hybridoma that produces an antibody, the antibody gene can be acquired by a known method using RNA extracted from the hybridoma.

When there is no hybridoma that produces an antibody, a hybridoma that produces an antibody may be prepared by known methods such as those described in, for example, Kohler and Milstein, Nature, vol. 256, p. 495-497, 1975. Alternatively, RNA obtained from peripheral blood or spleen of an animal such as a mouse or rabbit immunized with a predetermined antigen may be used. When RNA obtained from peripheral blood or spleen is used, cDNA may be synthesized from the RNA and a Fab phage library may be prepared from the obtained cDNA, as shown in Example 1 described later. Using this library, a gene encoding Fab can be acquired as an antibody gene by a phage display method or the like.

In the present embodiment, a cell containing an expression vector containing an ALP gene and an antibody gene is used. The expression vector has a promoter that enables protein expression in a host cell, and is not particularly limited as long as a desired gene can be inserted downstream of the promoter. The expression vector may be a plasmid vector or a viral vector. A commercially available expression vector may be used. If necessary, the expression vector may contain a gene other than the ALP gene and the antibody gene. Examples of such a gene include a gene encoding a peptide linker described later, a drug resistance gene, and the like.

In the present embodiment, the cell is not particularly limited as long as it can be used as a gene recombination expression system, and examples thereof include mammalian cells, insect cells, plant cells, yeast, *Escherichia coli*, and the like. By transforming or transfecting a cell with an expression vector containing an ALP gene and an antibody gene, the cell containing an expression vector can be obtained. Transformation and transfection can be performed by known methods depending on the type of expression vector. Examples of such a method include a lipofection method, a calcium phosphate method, an electroporation method, and the like. Commercially available transfection kits may be used.

The ALP gene and antibody gene are preferably incorporated into an expression vector so that a fusion protein of BIAP or S-AP and an antibody can be expressed. In the expression vector, the ALP gene may be incorporated upstream or downstream of the antibody gene. When the ALP gene is incorporated upstream of the antibody gene, an ALP fusion antibody is expressed in which a C-terminal amino acid residue of BIAP or S-AP and an N-terminal amino acid residue of the antibody are bound directly or via a peptide linker described later. When the ALP gene is incorporated downstream of the antibody gene, an ALP fusion antibody is expressed in which an N-terminal amino acid residue of BIAP or S-AP and a C-terminal amino acid residue of the antibody are bound directly or via a peptide linker described later.

When the antibody has all or part of a heavy chain and all or part of a light chain, like a full-length antibody or fragment such as Fab, the antibody gene includes a gene encoding all or part of the heavy chain (hereinafter, also referred to as "heavy chain gene") and a gene encoding all or a part of the light chain (hereinafter, also referred to as "light chain gene"). The heavy chain gene and the light chain gene may be incorporated into one expression vector so that each can be expressed independently, or they may be incorporated into two expression vectors separately. The ALP gene is preferably incorporated upstream or downstream of either the heavy chain gene or the light chain gene. As a result, a fusion protein of ALP and all or part of the heavy chain, or a fusion protein of ALP and all or part of the light chain is expressed.

In the present embodiment, the ALP gene and the antibody gene may be directly linked in the expression vector. In this case, an ALP fusion antibody in which BIAP or S-AP and the antibody are directly bound is expressed. In a further embodiment, a gene encoding a peptide linker (hereinafter, also referred to as "linker gene") may be further included between the ALP gene and the antibody gene. In this case, an ALP fusion antibody in which BIAP or S-AP and the antibody are bound via a peptide linker is expressed. The amino acid sequence of the peptide linker is not particularly limited as long as it does not affect antigen-binding ability and ALP activity of the antibody. Length of the peptide linker is not particularly limited, but is, for example, 3 to 20 amino acid residues. In the present embodiment, the peptide linker is preferably any one selected from GS1, GS2, GS3, EK1, EK2 and EK3 having each of the following amino acid sequences.

```
GS1:
                                    (SEQ ID NO: 5)
Gly-Gly-Gly-Gly-Ser

GS2:
                                    (SEQ ID NO: 6)
(Gly-Gly-Gly-Gly-Ser)2

GS3:
                                    (SEQ ID NO: 7)
(Gly-Gly-Gly-Gly-Ser)3

EK1:
                                    (SEQ ID NO: 8)
Glu-Ala-Ala-Ala-Lys

EK2:
                                    (SEQ ID NO: 9)
(Glu-Ala-Ala-Ala-Lys)2

EK3:
                                    (SEQ ID NO: 10)
(Glu-Ala-Ala-Ala-Lys)3
```

Figure 1B:
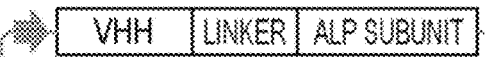
FIG. 1B shows schematic diagrams of constitution examples of expression vectors.
Figure 1B:
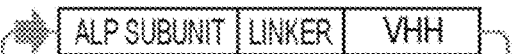
Figure 1B:
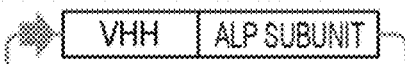
Figure 1B:
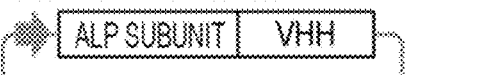
Figure 1C:
FIG. 1C shows schematic diagrams of constitution examples of expression vectors.
Figure 1C:
Figure 1C:
Figure 1C:
Figure 1C:
Figure 1C:
Figure 1C:
Figure 1C:

Constitution examples of expression vectors containing an ALP gene and an antibody gene in the present embodiment will be described with reference to FIGS. 1A to 1C. In FIGS. 1A to 1C, the expression vector is exemplified as plasmid DNA, and an arrow indicates a promoter. In the figures, "Fd(HC)" represents a gene encoding Fd. Fd is a heavy chain portion of Fab. In the figures, "LC" represents a gene encoding a light chain, "linker" represents a linker gene, and "ALP subunit" represents an ALP gene. Whereas ALP as an enzyme usually exists in the form of a homodimer, the "ALP subunit" as a protein is intended to refer to monomeric ALP.

FIG. 1A shows expression vectors in which a gene encoding Fd or a light chain and an ALP gene are linked directly or via a gene encoding a peptide linker. FIG. 1B shows expression vectors in which a gene encoding VHH and an ALP gene are linked directly or via a gene encoding a peptide linker. FIG. 1C shows expression vectors further containing a gene encoding a light chain or Fd in each expression vector shown in FIG. 1A. However, the expression vectors used in the present disclosure are not limited to these examples. For example, a full-length heavy chain or a gene encoding Fd' may be used instead of the gene encoding Fd. A gene encoding scFv may be used instead of the gene encoding VHH.

The expression vector of Constitution Example 1-1 contains the gene encoding Fd, the linker gene and the ALP gene in this order downstream of the promoter. This expression vector expresses a fusion protein in which a C-terminal amino acid residue of Fd and an N-terminal amino acid residue of the ALP subunit are bound via a peptide linker. By transforming or transfecting a cell with the expression vector of Constitution Example 1-1 and the expression vector containing the gene encoding a light chain, a Fab containing the fusion protein and the light chain is obtained as an ALP fusion antibody.

The expression vector of Constitution Example 1-2 contains the gene encoding a light chain, the linker gene and the ALP gene in this order downstream of the promoter. This expression vector expresses a fusion protein in which a C-terminal amino acid residue of the light chain and an N-terminal amino acid residue of the ALP subunit are bound via a peptide linker. By transforming or transfecting a cell with the expression vector of Constitution Example 1-2 and the expression vector containing the gene encoding Fd, a Fab containing the fusion protein and Fd is obtained as an ALP fusion antibody.

The expression vector of Constitution Example 1-3 contains the gene encoding Fd and the ALP gene in this order downstream of the promoter. This expression vector expresses a fusion protein in which a C-terminal amino acid residue of Fd and an N-terminal amino acid residue of the ALP subunit are directly bound. By transforming or transfecting a cell with the expression vector of Constitution Example 1-3 and the expression vector containing the gene encoding a light chain, a Fab containing the fusion protein and the light chain is obtained as an ALP fusion antibody.

The expression vector of Constitution Example 1-4 contains the gene encoding a light chain and the ALP gene in this order downstream of the promoter. This expression vector expresses a fusion protein in which a C-terminal amino acid residue of the light chain and an N-terminal amino acid residue of the ALP subunit are directly bound. By transforming or transfecting a cell with the expression vector of Constitution Example 1-4 and the expression vector containing the gene encoding Fd, a Fab containing the fusion protein and Fd is obtained as an ALP fusion antibody.

The expression vector of Constitution Example 2-1 contains the ALP gene, the linker gene and the gene encoding Fd in this order downstream of the promoter. This expression vector expresses a fusion protein in which an N-terminal amino acid residue of Fd and a C-terminal amino acid residue of the ALP subunit are bound via a peptide linker. By transforming or transfecting a cell with the expression vector of Constitution Example 2-1 and the expression vector containing the gene encoding a light chain, a Fab containing the fusion protein and the light chain is obtained as an ALP fusion antibody.

The expression vector of Constitution Example 2-2 contains the ALP gene, the linker gene and the gene encoding a light chain in this order downstream of the promoter. This expression vector expresses a fusion protein in which an N-terminal amino acid residue of the light chain and a C-terminal amino acid residue of the ALP subunit are bound via a peptide linker. By transforming or transfecting a cell with the expression vector of Constitution Example 2-2 and the expression vector containing the gene encoding Fd, a Fab containing the fusion protein and Fd is obtained as an ALP fusion antibody.

The expression vector of Constitution Example 2-3 contains the ALP gene and the gene encoding Fd in this order downstream of the promoter. This expression vector expresses a fusion protein in which an N-terminal amino acid residue of Fd and a C-terminal amino acid residue of the ALP subunit are directly bound. By transforming or transfecting a cell with the expression vector of Constitution Example 2-3 and the expression vector containing the gene encoding a light chain, a Fab containing the fusion protein and the light chain is obtained as an ALP fusion antibody.

The expression vector of Constitution Example 2-4 contains the ALP gene and the gene encoding a light chain in this order downstream of the promoter. This expression vector expresses a fusion protein in which an N-terminal amino acid residue of the light chain and a C-terminal amino acid residue of the ALP subunit are directly bound. By transforming or transfecting a cell with the expression vector of Constitution Example 2-4 and the expression vector containing the gene encoding Fd, a Fab containing the fusion protein and Fd is obtained as an ALP fusion antibody.

The expression vector of Constitution Example 3-1 contains the gene encoding VHH, the linker gene and the ALP gene in this order downstream of the promoter. By transforming or transfecting a cell with the expression vector of Constitution Example 3-1, an ALP fusion antibody in which a C-terminal amino acid residue of VHH and an N-terminal amino acid residue of the ALP subunit were bound via a peptide linker is obtained.

The expression vector of Constitution Example 3-2 contains the gene encoding VHH and the ALP gene in this order downstream of the promoter. By transforming or transfecting a cell using the expression vector of Constitution Example 3-2, an ALP fusion antibody in which a C-terminal amino acid residue of VHH and an N-terminal amino acid residue of the ALP subunit were directly bound is obtained.

The expression vector of Constitution Example 3-3 contains the ALP gene, the linker gene and the gene encoding VHH in this order downstream of the promoter. By transforming or transfecting a cell with the expression vector of Constitution Example 3-3, an ALP fusion antibody in which an N-terminal amino acid residue of VHH and a C-terminal amino acid residue of the ALP subunit were bound via a peptide linker is obtained.

The expression vector of Constitution Example 3-4 contains the ALP gene and the gene encoding VHH in this order downstream of the promoter. By transforming or transfecting a cell using the expression vector of Constitution Example 3-4, an ALP fusion antibody in which an N-terminal amino acid residue of VHH and a C-terminal amino acid residue of the ALP subunit were directly bound is obtained.

The expression vector of Constitution Example 4-1 is an expression vector containing two promoters, which contains a gene encoding Fd, a linker gene and an ALP gene in this order downstream of one promoter, and contains a gene encoding a light chain downstream of the other promoter. By transforming or transfecting a cell with the expression vector of Constitution Example 4-1, a Fab containing a fusion protein in which a C-terminal amino acid residue of Fd and an N-terminal amino acid residue of the ALP subunit are bound via a peptide linker and the light chain is obtained as an ALP fusion antibody.

The expression vector of Constitution Example 4-2 is an expression vector containing two promoters, which contains a gene encoding a light chain, a linker gene and an ALP gene in this order downstream of one promoter, and contains a gene encoding Fd downstream of the other promoter. By transforming or transfecting a cell with the expression vector of Constitution Example 4-2, a Fab containing a fusion protein in which a C-terminal amino acid residue of the light chain and an N-terminal amino acid residue of the ALP subunit are bound via a peptide linker and Fd is obtained as an ALP fusion antibody.

The expression vector of Constitution Example 4-3 is an expression vector containing two promoters, which contains a gene encoding Fd and an ALP gene in this order downstream of one promoter, and contains a gene encoding a light chain downstream of the other promoter. By transforming or transfecting a cell with the expression vector of Constitution Example 4-3, a Fab containing a fusion protein in which a C-terminal amino acid residue of Fd and an N-terminal amino acid residue of the ALP subunit are directly bound and the light chain is obtained as an ALP fusion antibody.

The expression vector of Constitution Example 4-4 is an expression vector containing two promoters, which contains a gene encoding a light chain and an ALP gene in this order downstream of one promoter, and contains a gene encoding Fd downstream of the other promoter. By transforming or transfecting a cell with the expression vector of Constitution Example 4-4, a Fab containing a fusion protein in which a C-terminal amino acid residue of the light chain and an N-terminal amino acid residue of the ALP subunit are directly bound and Fd is obtained as an ALP fusion antibody.

The expression vector of Constitution Example 5-1 is an expression vector containing two promoters, which contains an ALP gene, a linker gene and a gene encoding Fd in this order downstream of one promoter, and contains a gene encoding a light chain downstream of the other promoter. By transforming or transfecting a cell with the expression vector of Constitution Example 5-1, a Fab containing a fusion protein in which an N-terminal amino acid residue of Fd and a C-terminal amino acid residue of the ALP subunit are bound via a peptide linker and the light chain is obtained as an ALP fusion antibody.

The expression vector of Constitution Example 5-2 is an expression vector containing two promoters, which contains an ALP gene, a linker gene and a gene encoding a light chain in this order downstream of one promoter, and contains a gene encoding Fd downstream of the other promoter. By transforming or transfecting a cell with the expression vector of Constitution Example 5-2, a Fab containing a fusion protein in which an N-terminal amino acid residue of the light chain and a C-terminal amino acid residue of the ALP subunit are bound via a peptide linker and Fd is obtained as an ALP fusion antibody.

The expression vector of Constitution Example 5-3 is an expression vector containing two promoters, which contains an ALP gene and a gene encoding Fd in this order downstream of one promoter, and contains a gene encoding a light chain downstream of the other promoter. By transforming or transfecting a cell with the expression vector of Constitution Example 5-3, a Fab containing a fusion protein in which an N-terminal amino acid residue of Fd and a C-terminal amino acid residue of the ALP subunit are directly bound and the light chain is obtained as an ALP fusion antibody.

The expression vector of Constitution Example 5-4 is an expression vector containing two promoters, which contains an ALP gene and a gene encoding a light chain in this order downstream of one promoter, and contains a gene encoding Fd downstream of the other promoter. By transforming or transfecting a cell with the expression vector of Constitution Example 5-4, a Fab containing a fusion protein in which an N-terminal amino acid residue of the light chain and a C-terminal amino acid residue of the ALP subunit are directly bound and Fd is obtained as an ALP fusion antibody.

ALP is known to be a type of zinc enzyme. In the present embodiment, it is desirable to culture cells containing an expression vector containing an ALP gene and an antibody gene in a medium containing a zinc ion. Zinc ion concentration in the medium is preferably 0.01 mM or more, more preferably 0.05 mM or more, and further preferably 0.07 mM or more. The zinc ion concentration is preferably 0.25 mM or less, more preferably 0.20 mM or less, and further preferably 0.15 mM or less, because too high a zinc ion concentration in the medium may affect cell culture. The cell can be appropriately cultured by a known culture method according to the cell to be used. The medium containing a zinc ion can be prepared by adding a compound capable of supplying a zinc ion or a solution thereof to a medium suitable for the cell to be used. Such a compound is preferably a salt of zinc and an inorganic or an organic acid. Examples of such a salt include zinc chloride, zinc sulfate, zinc acetate, and the like. In the present embodiment, when a salt of zinc and an inorganic acid or an organic acid is added to the medium, the concentration of the zinc ion in the medium may be expressed by final concentration of the salt.

As shown in Test Example 2, even when an ALP fusion antibody was expressed in a cell and then cultured in a medium containing a zinc ion, ALP in the obtained ALP fusion antibody showed no activity. Therefore, in the present embodiment, it is preferable to add a zinc ion to a medium or replace it with a medium containing a zinc ion, during a period from transforming or transfecting a cell using an expression vector until an ALP fusion antibody is expressed in the cell.

In the production method of the present embodiment, the ALP fusion antibody is recovered from the above cell. As a result, the ALP fusion antibody of the present embodiment in which BIAP or S-AP and the antibody are bound directly or via a peptide linker is obtained. For example, a cell expressing the ALP fusion antibody may be dissolved in a solution containing a suitable solubilizer to recover the ALP fusion antibody liberated in the solution. When the cell secretes the ALP fusion antibody into a medium, a culture supernatant is recovered. The liberated ALP fusion antibody can be recovered by a known method such as affinity chromatography. If necessary, the recovered ALP fusion antibody may be purified by a method known in the art such as gel filtration.

In the ALP fusion antibody of the present embodiment, a C-terminal amino acid residue of ALP and an N-terminal amino acid residue of the antibody may be bound directly or via a peptide linker. Alternatively, in the ALP fusion antibody of the present embodiment, an N-terminal amino acid residue of ALP and a C-terminal amino acid residue of the amino acid sequence of the antibody may be bound directly or via a peptide linker.

As mentioned above, ALP as an enzyme usually exists in the form of a homodimer. Therefore, in the present embodiment, the ALP contained in the ALP fusion antibody may contain two subunits. The two subunits may form a dimer. In this case, the antibody contained in the ALP fusion antibody may be bound to one of the two subunits or to both. That is, the ALP fusion antibody of the present embodiment contains an ALP subunit to which an antibody is bound and an ALP subunit to which an antibody is not bound, or contains two ALP subunits to which an antibody is bound. The ALP subunit to which an antibody is not bound can be obtained by an expression vector containing an ALP gene.

Figure 2A:
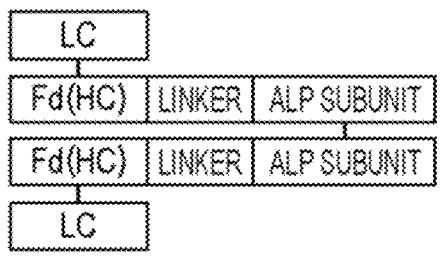
FIG. 2A shows schematic diagrams of examples of the ALP fusion antibodies of the present embodiment.
Figure 2A:
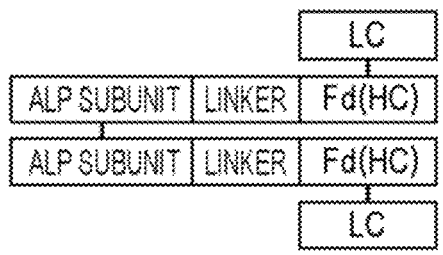
Figure 2A:
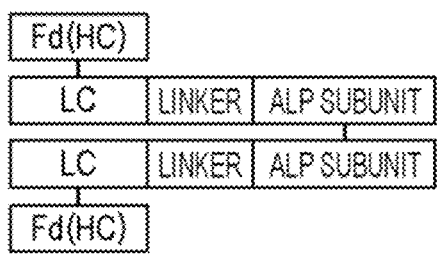
Figure 2A:
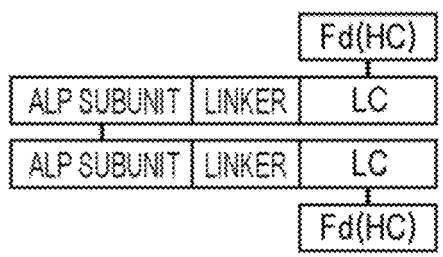
Figure 2A:
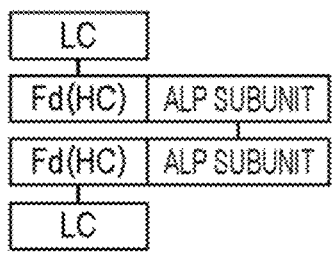
Figure 2A:
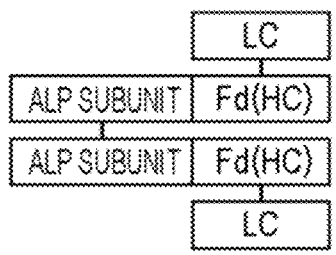
Figure 2A:
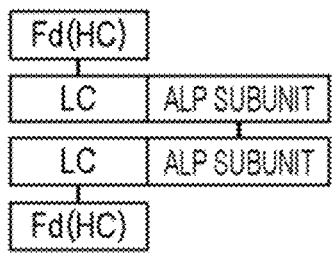
Figure 2A:
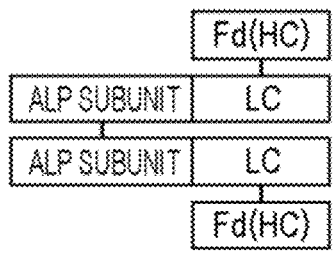
Figure 2B:
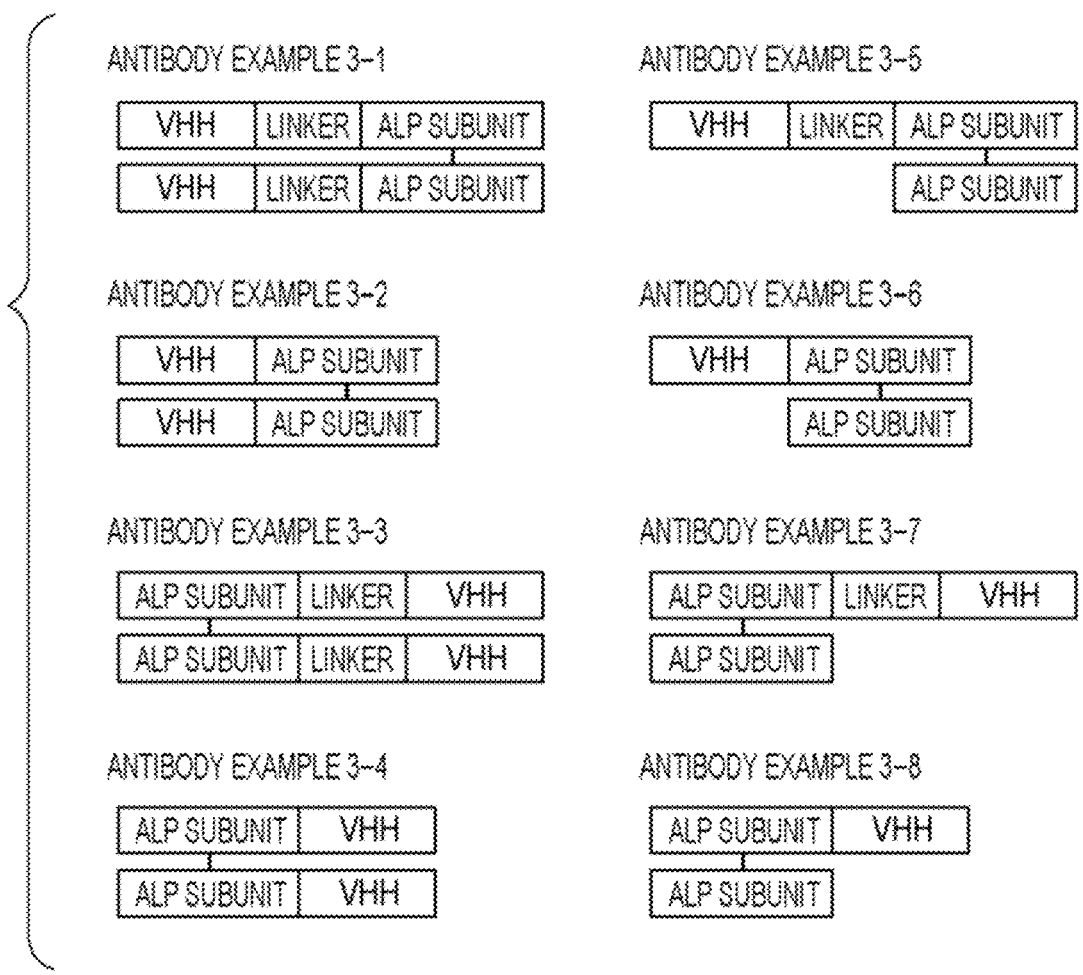
FIG. 2B shows schematic diagrams of examples of the ALP fusion antibodies of the present embodiment.
Figure 2C:
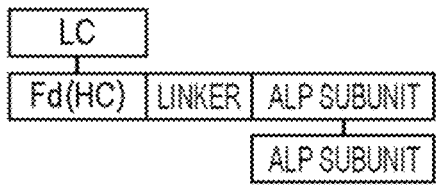
FIG. 2C shows schematic diagrams of examples of the ALP fusion antibodies of the present embodiment.
Figure 2C:
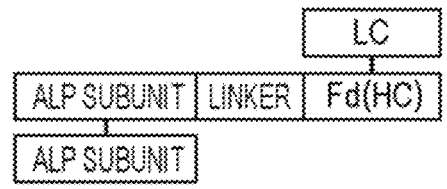
Figure 2C:
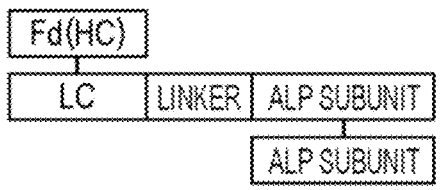
Figure 2C:
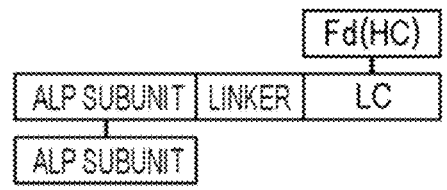
Figure 2C:
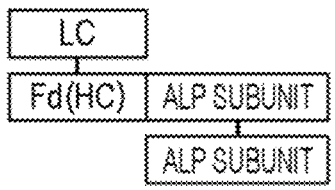
Figure 2C:
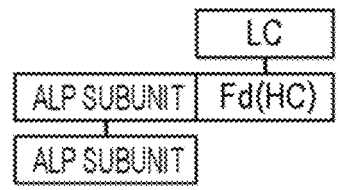
Figure 2C:
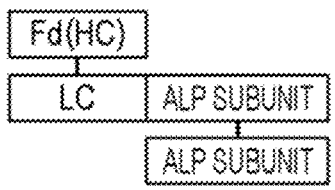
Figure 2C:
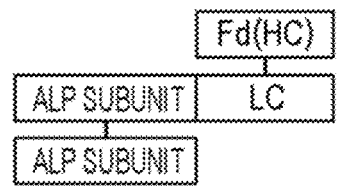

Examples of the ALP fusion antibody of the present embodiment will be described with reference to FIGS. 2A to 2C. In FIGS. 2A to 2C, "Fd(HC)" represents Fd, "LC" represents a light chain, "linker" represents a peptide linker, and "ALP subunit" represents monomeric ALP. In the figures, a line between Fd(HC) and LC represents a disulfide bond, and a line between ALP subunits represents formation of a dimer. However, the ALP fusion antibody of the present embodiment is not limited to these examples. For example, Fd in the ALP fusion antibody may be a full-length heavy chain or Fd'. VHH in the ALP fusion antibody may be scFv.

In the ALP fusion antibody of Antibody Example 1-1, two molecules of ALP fusion Fab, in which a C-terminal amino acid residue of the heavy chain portion (Fd) and an N-terminal amino acid residue of the ALP subunit are bound via a peptide linker, form a complex by dimer formation between the ALP subunits. In the ALP fusion antibody of Antibody Example 1-2, two molecules of ALP fusion Fab, in which a C-terminal amino acid residue of a light chain and an N-terminal amino acid residue of the ALP subunit are bound via a peptide linker, form a complex by dimer formation between the ALP subunits.

In the ALP fusion antibody of Antibody Example 1-3, two molecules of ALP fusion Fab, in which a C-terminal amino acid residue of the heavy chain portion (Fd) and an N-terminal amino acid residue of the ALP subunit are directly bound, form a complex by dimer formation between the ALP subunits. In the ALP fusion antibody of Antibody Example 1-4, two molecules of ALP fusion Fab, in which a C-terminal amino acid residue of the light chain and an N-terminal amino acid residue of the ALP subunit are directly bound, form a complex by dimer formation between the ALP subunits.

In the ALP fusion antibody of Antibody Example 2-1, two molecules of ALP fusion Fab, in which an N-terminal amino acid residue of the heavy chain portion (Fd) and a C-terminal amino acid residue of the ALP subunit are bound via a peptide linker, form a complex by dimer formation between the ALP subunits. In the ALP fusion antibody of Antibody Example 2-2, two molecules of ALP fusion Fab, in which an N-terminal amino acid residue of the light chain and a C-terminal amino acid residue of the ALP subunit are bound via a peptide linker, form a complex by dimer formation between the ALP subunits.

In the ALP fusion antibody of Antibody Example 2-3, two molecules of ALP fusion Fab, in which an N-terminal amino acid residue of the heavy chain portion (Fd) and a C-terminal amino acid residue of the ALP subunit are directly bound, form a complex by dimer formation between the ALP subunits. In the ALP fusion antibody of Antibody Example 2-4, two molecules of ALP fusion Fab, in which an N-terminal amino acid residue of the light chain and a C-terminal amino acid residue of the ALP subunit are directly bound, form a complex by dimer formation between the ALP subunits.

In the ALP fusion antibody of Antibody Example 3-1, two molecules of ALP fusion VHH, in which a C-terminal amino acid residue of VHH and an N-terminal amino acid residue of the ALP subunit are bound via a peptide linker, form a complex by dimer formation between the ALP subunits. In the ALP fusion antibody of Antibody Example 3-2, two molecules of ALP fusion VHH, in which a C-terminal amino acid residue of VHH and an N-terminal amino acid residue of the ALP subunit are directly bound, form a complex by dimer formation between the ALP subunits.

In the ALP fusion antibody of Antibody Example 3-3, two molecules of ALP fusion VHH, in which an N-terminal amino acid residue of VHH and a C-terminal amino acid residue of the ALP subunit are bound via a peptide linker, form a complex by dimer formation between the ALP subunits. In the ALP fusion antibody of Antibody Example 3-4, two molecules of ALP fusion VHH, in which an N-terminal amino acid residue of VHH and a C-terminal amino acid residue of the ALP subunit are directly bound, form a complex by dimer formation between the ALP subunits.

In the ALP fusion antibody of Antibody Example 3-5, ALP fusion VHH, in which a C-terminal amino acid residue of VHH and an N-terminal amino acid residue of the ALP subunit are bound via a peptide linker, and the ALP subunit to which an antibody is not bound form a dimer between the ALP subunits. The ALP fusion antibody of Antibody Example 3-5 can be obtained by transforming or transfecting a cell using the expression vector of Constitution Example 3-1 and the expression vector containing an ALP gene.

In the ALP fusion antibody of Antibody Example 3-6, ALP fusion VHH, in which a C-terminal amino acid residue of VHH and an N-terminal amino acid residue of the ALP subunit are directly bound, and the ALP subunit to which an antibody is not bound form a dimer between the ALP subunits. The ALP fusion antibody of Antibody Example 3-6 can be obtained by transforming or transfecting a cell using the expression vector of Constitution Example 3-2 and the expression vector containing an ALP gene.

In the ALP fusion antibody of Antibody Example 3-7, ALP fusion VHH, in which an N-terminal amino acid residue of VHH and a C-terminal amino acid residue of the ALP subunit are bound via a peptide linker, and the ALP subunit to which an antibody is not bound form a dimer between the ALP subunits. The ALP fusion antibody of Antibody Example 3-7 can be obtained by transforming or transfecting a cell using the expression vector of Constitution Example 3-3 and the expression vector containing an ALP gene.

In the ALP fusion antibody of Antibody Example 3-8, ALP fusion VHH, in which an N-terminal amino acid residue of VHH and a C-terminal amino acid residue of the ALP subunit are directly bound, and the ALP subunit to which an antibody is not bound form a dimer between the ALP subunits. The ALP fusion antibody of Antibody Example 3-8 can be obtained by transforming or transfecting a cell using the expression vector of Constitution Example 3-4 and the expression vector containing an ALP gene.

In the ALP fusion antibody of Antibody Example 4-1, ALP fusion Fab, in which a C-terminal amino acid residue of the heavy chain portion (Fd) and an N-terminal amino acid residue of the ALP subunit are bound via a peptide linker, and the ALP subunit to which an antibody is not bound form a dimer between the ALP subunits. The ALP fusion antibody of Antibody Example 4-1 can be obtained, for example, by transforming or transfecting a cell using the expression vector of Constitution Example 1-1, the expression vector containing the gene encoding a light chain, and the expression vector containing an ALP gene.

In the ALP fusion antibody of Antibody Example 4-2, ALP fusion Fab, in which a C-terminal amino acid residue of the light chain and an N-terminal amino acid residue of the ALP subunit are bound via a peptide linker, and the ALP subunit to which an antibody is not bound form a dimer between the ALP subunits. The ALP fusion antibody of Antibody Example 4-2 can be obtained, for example, by transforming or transfecting a cell using the expression vector of Constitution Example 1-2, the expression vector containing the gene encoding Fd, and the expression vector containing an ALP gene.

In the ALP fusion antibody of Antibody Example 4-3, ALP fusion Fab, in which a C-terminal amino acid residue of the heavy chain portion (Fd) and an N-terminal amino acid residue of the ALP subunit are directly bound, and the ALP subunit to which an antibody is not bound form a dimer between the ALP subunits. The ALP fusion antibody of Antibody Example 4-3 can be obtained, for example, by transforming or transfecting a cell using the expression vector of Constitution Example 1-3, the expression vector containing the gene encoding a light chain, and the expression vector containing an ALP gene.

In the ALP fusion antibody of Antibody Example 4-4, ALP fusion Fab, in which a C-terminal amino acid residue of the light chain and an N-terminal amino acid residue of the ALP subunit are directly bound, and the ALP subunit to which an antibody is not bound form a dimer between the ALP subunits. The ALP fusion antibody of Antibody Example 4-4 can be obtained, for example, by transforming or transfecting a cell using the expression vector of Constitution Example 1-4, the expression vector containing the gene encoding Fd, and the expression vector containing an ALP gene.

In the ALP fusion antibody of Antibody Example 5-1, ALP fusion Fab, in which an N-terminal amino acid residue of the heavy chain portion (Fd) and a C-terminal amino acid residue of the ALP subunit are bound via a peptide linker, and the ALP subunit to which an antibody is not bound form a dimer between the ALP subunits. The ALP fusion antibody of Antibody Example 5-1 can be obtained, for example, by transforming or transfecting a cell using the expression vector of Constitution Example 2-1, the expression vector containing the gene encoding a light chain, and the expression vector containing an ALP gene.

In the ALP fusion antibody of Antibody Example 5-2, ALP fusion Fab, in which an N-terminal amino acid residue of the light chain and a C-terminal amino acid residue of the ALP subunit are bound via a peptide linker, and the ALP subunit to which an antibody is not bound form a dimer between the ALP subunits. The ALP fusion antibody of Antibody Example 5-2 can be obtained, for example, by transforming or transfecting a cell using the expression vector of Constitution Example 2-2, the expression vector containing the gene encoding Fd, and the expression vector containing an ALP gene.

In the ALP fusion antibody of Antibody Example 5-3, ALP fusion Fab, in which an N-terminal amino acid residue of the heavy chain portion (Fd) and a C-terminal amino acid residue of the ALP subunit are directly bound, and the ALP subunit to which an antibody is not bound form a dimer between the ALP subunits. The ALP fusion antibody of Antibody Example 5-3 can be obtained, for example, by transforming or transfecting a cell using the expression vector of Constitution Example 2-3, the expression vector containing the gene encoding a light chain, and the expression vector containing an ALP gene.

In the ALP fusion antibody of Antibody Example 5-4, ALP fusion Fab, in which an N-terminal amino acid residue of the light chain and a C-terminal amino acid residue of the ALP subunit are directly bound, and the ALP subunit to which an antibody is not bound form a dimer between the ALP subunits. The ALP fusion antibody of Antibody Example 5-4 can be obtained, for example, by transforming or transfecting a cell using the expression vector of Constitution Example 2-4, the expression vector containing the gene encoding Fd, and the expression vector containing an ALP gene.

The ALP fusion antibody of the present embodiment can be used to detect a test substance in immunoassay. Therefore, one embodiment is an immunoassay reagent containing the ALP fusion antibody. The type of immunoassay is not particularly limited. For example, the type of immunoassay can be selected as appropriate from known immunoassay methods such as ELISA, Western blotting, and immune complex transfer method (see Japanese Laid-Open Patent Publication No. H1-254868). Among them, the ELISA is preferred. The ELISA may be any of a sandwich method, a competitive method, a direct method, an indirect method, and the like.

In the present embodiment, a form of the reagent is not particularly limited, and may be solid (for example, powder, crystal, freeze-dried product, or the like) or liquid (for example, solution, suspension, emulsion, or the like). When the reagent is a liquid, a solvent is not particularly limited as long as the ALP fusion antibody of the present embodiment can be dissolved and stored. Examples of the solvent include water, physiological saline, phosphate buffered saline (PBS), Tris buffered saline (TBS), Good's buffer, and the like. Examples of the Good's buffers include MES, Bis-Tris, ADA, PIPES, Bis-Tris-Propane, ACES, MOPS, MOPSO, BES, TES, HEPES, HEPPS, Tricine, Tris, Bicine, TAPS, and the like.

The immunoassay reagent of the present embodiment may contain known additives. Examples of the additive include protein stabilizers such as bovine serum albumin (BSA), preservatives such as sodium azide, inorganic salts such as sodium chloride, and the like.

Figure 3:
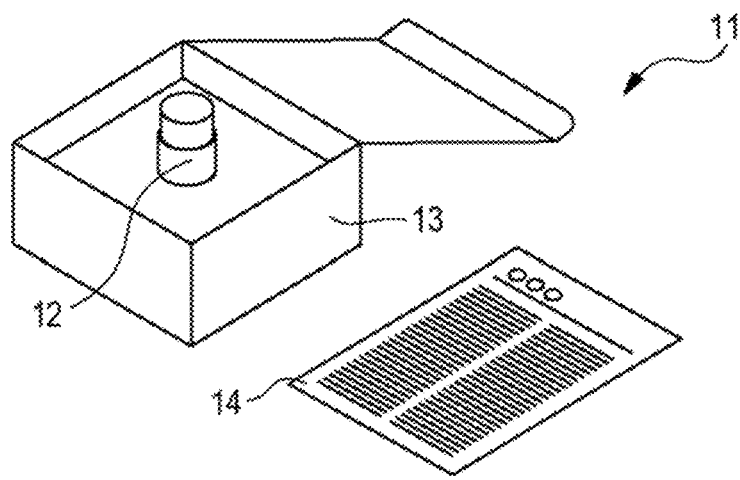
FIG. 3 is a schematic diagram showing an example of an immunoassay reagent kit of the present embodiment.

In the present embodiment, a container containing an immunoassay reagent may be packed in a box and provided to the user as a reagent kit. The box may contain an attached document. Composition, usage, storage method, etc. of the immunoassay reagent may be described in the attached document. FIG. 3 shows an example of the reagent kit. In FIG. 3, 11 denotes a reagent kit of the present embodiment, 12 denotes a first container containing an immunoassay reagent containing an ALP fusion antibody of the present embodiment, 13 denotes a packing box, and 14 denotes an attached document.

When the immunoassay is a measurement by sandwich ELISA, a capture substance that specifically binds to a test substance is used in addition to the ALP fusion antibody of the present embodiment. Therefore, a further embodiment is an immunoassay reagent kit containing a first reagent containing the ALP fusion antibody and a second reagent containing a capture substance that specifically binds to a test substance. Details of the first reagent are the same as those described for the immunoassay reagent of the present embodiment.

The capture substance that specifically binds to a test substance refers to a substance that captures a test substance on a solid phase by being immobilized on the solid phase. The type of the capture substance is not particularly limited, and can be appropriately selected depending on the type of the test substance. Examples of the capture substance include antibodies, antigens, oligonucleotide probes, receptors, ligands that bind to the receptors, aptamers, and the like. Hereinafter, an antibody used as a capture substance is also referred to as "capture antibody". The capture antibody may be either a monoclonal antibody or a polyclonal antibody, but is preferably a monoclonal antibody. When the capture antibody is a monoclonal antibody, an epitope recognized by the capture antibody is preferably different from an epitope recognized by the ALP fusion antibody of the present embodiment.

In the immunoassay reagent kit of the present embodiment, the ALP fusion antibody of the present embodiment contained in the first reagent is preferably used as a detection antibody in the sandwich ELISA. The detection antibody refers to an antibody that specifically binds to a test substance and has a labeling substance, and provides an antibody that provides a detectable signal via the labeling substance. It is preferable that the detection antibody is not immobilized on a solid phase.

Figure 4:
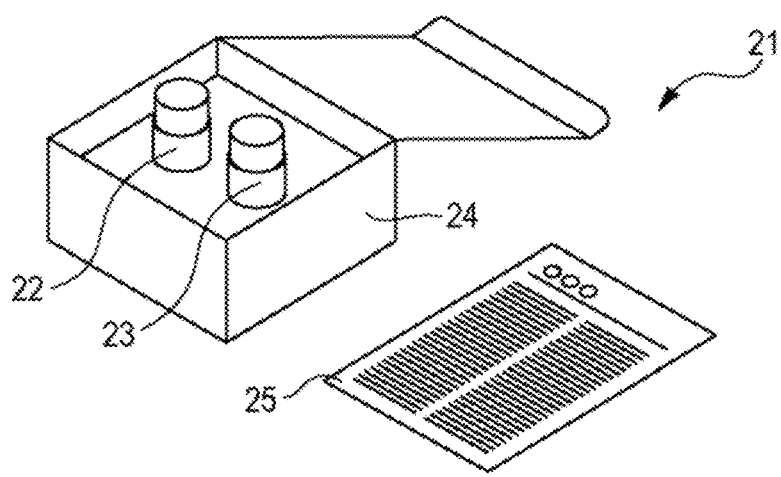
FIG. 4 is a schematic diagram showing an example of an immunoassay reagent kit of the present embodiment.

In the present embodiment, containers containing each of the first reagent and the second reagent may be packed in a box and provided to the user as a reagent kit. The box may contain an attached document. Configuration, composition of each reagent, usage, storage method, etc. of the immunoassay reagent kit of the present embodiment may be described in the attached document. FIG. 4 shows an example of the reagent kit. In FIG. 4, 21 denotes a reagent kit of the present embodiment, 22 denotes a first container containing a first reagent containing an ALP fusion antibody of the present embodiment, 23 denotes a second container containing a second reagent containing a capture substance that specifically binds to a test substance, 24 denotes a packing box, and 25 denotes an attached document.

The immunoassay reagent kit of the present embodiment may further contain a solid phase for immobilizing the capture substance. The solid phase may be any insoluble carrier capable of immobilizing the capture substance. The material of the solid phase is not particularly limited. For example, the material can be selected from organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include microplates, microtubes, test tubes, particles, membranes, and the like. Among them, microplates and particles (particularly magnetic particles) are preferable.

The immunoassay reagent kit of the present embodiment may further contain a substrate of ALP. Examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13.7]decan]-4-yl)phenyl phosphate) and CSPD (registered trademark) (disodium 3-(4-methoxyspiro[1,2-dioxetane-3, 2-(5'-chloro)tricyclo[3.3.1.13.7]decan]-4-yl)phenyl phosphate), and chromogenic substrates such as 5-bromo-4-chloro-3-indolyl phosphate (BCIP), disodium 5-bromo-6-chloro-indolyl phosphate and p-nitrophenyl phosphate.

The immunoassay reagent kit of the present embodiment may further contain a calibrator of the test substance. Examples of the calibrator include a calibrator for quantification of a test substance. This calibrator may include, for example, a buffer solution containing no test substance (negative control) and a buffer solution containing test substance at a known concentration. When the test substance is a protein, the test substance contained in the calibrator may be a recombinant protein or a polypeptide synthesized based on the amino acid sequence of the test substance.

A further embodiment is an immunoassay method using the ALP fusion antibody. This measurement method includes, for example, measuring a test substance in a sample using the ALP fusion antibody of the present embodiment. The test substance is not particularly limited as long as it is a substance to which the ALP fusion antibody of the present embodiment can specifically bind. Examples of the test substance include proteins, nucleic acids, polysaccharides, lipids, haptens, compounds, bacteria, viruses, and the like. The sample is not particularly limited as long as it contains a test substance. Examples of the sample include biological samples such as blood and lymph fluid, excreta such as urine and feces, environmental samples such as river water, sea water and soil, and the like.

As an example, the case of measuring by sandwich ELISA will be described below. In this example, the ALP fusion antibody of the present embodiment is used as a detection antibody. First, a complex containing a test substance, a capture substance that specifically binds to the test substance, and the ALP fusion antibody (detection antibody) of the present embodiment is formed on a solid phase. The complex can be formed by mixing a sample that may contain a test substance, a capture substance, and a detection antibody. Then, a solution containing the complex is brought into contact with a solid phase capable of immobilizing the capture substance, whereby the complex can be formed on the solid phase. Alternatively, a solid phase preliminarily immobilized with the capture substance may be used. That is, a solid phase immobilized with the capture substance, the sample that may contain a test substance, and the detection antibody are brought into contact with each other, whereby the complex can be formed on the solid phase. Moreover, the test substance contained in the sample can be measured by detecting the complex formed on the solid phase by a method known in the art. In the present embodiment, the test substance in the sample can be measured by detecting a signal generated by ALP contained in the detection antibody.

The mode of immobilization of the capture substance on the solid phase is not particularly limited. For example, the capture substance and the solid phase may be bound directly, or the capture substance and the solid phase may be indirectly bound via another substance. Examples of the direct binding include physical adsorption and the like. Examples of the indirect bond include a bond via a combination of biotin or its analog and a biotin-binding site. In this case, by preliminarily modifying the capture substance with biotin or its analog and previously binding a biotin-binding site to the solid phase, the capture substance and the solid phase can be indirectly bound via the bond between the biotin or its analog and the biotin-binding site. The biotin and its analogs include biotin and biotin analogs such as desthiobiotin. The biotin-binding sites include avidin and avidin analogs such as streptavidin and tamavidin (registered trademark).

In the present embodiment, B/F (Bound/Free) separation for removing an unreacted free component not forming a complex may be performed between formation of the complex and detection of the complex. The unreacted free component refers to a component not constituting a complex. Examples thereof include capture substances not bound to the test substance, detection antibodies, and the like. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet, which is preferable from the viewpoint of automation. After removing the unreacted free component, the solid phase capturing the complex may be washed with a suitable aqueous medium such as PBS.

As used herein, the phrase "detecting a signal" includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of a signal quantitatively or semi-quantitatively.

Methods for detecting a signal themselves are known in the art. In the present embodiment, signals such as light and color generated by reacting the complex on the solid phase with the substrate of ALP can be measured by using a known apparatus such as a spectrophotometer. The substrate for ALP is as described above.

The detection result of the signal can be used as the measurement result of the test substance. For example, when quantitatively detecting the intensity of a signal, a measured value of the signal intensity itself or a value acquired from the measured value can be used as the measurement result of the test substance. Examples of the value acquired from the measured value of the signal intensity include a value obtained by subtracting the measured value of a negative control sample or the background value from the measured value, and the like. The measured value of the signal intensity may be applied to a calibration curve to determine the amount or concentration value of the test substance. The negative control sample can be appropriately selected, and examples thereof include a sample known not to contain a test substance.

In the present embodiment, it is preferable to measure the test substance in the sample by a sandwich ELISA method using a capture antibody immobilized on magnetic particles and the ALP fusion antibody (detection antibody) of the present embodiment. In this case, measurement may be carried out using a commercially available fully automated immunoassay system such as HISCL series (manufactured by Sysmex Corporation).

Hereinafter, the present disclosure will be described in more detail by examples, but the present disclosure is not limited to these examples.

EXAMPLES

[Example 1] Preparation of Bovine Small Intestine-Derived ALP Fusion Antibody

A fusion protein in which rabbit antibody Fab and bovine small intestine-derived ALP subunit were bound was prepared. The fusion protein becomes an ALP fusion antibody having two molecules of Fab by forming a dimer of ALP subunits. This corresponds to the ALP fusion antibody having a structure shown in Antibody Example 1-1 above.
(1) Preparation of Expression Vector
(1.1) Acquisition of Gene of Rabbit Antibody Lymphocytes were acquired from peripheral blood of a rabbit immunized with CD80, and mRNA was extracted from the lymphocytes to synthesize cDNA. The obtained cDNA was amplified using a known primer for cloning an antibody gene to prepare a Fab phage library. Using the obtained library, a Fab clone of a rabbit anti-CD80 antibody was obtained by a known Fab phage display method and biopanning (see Lang I M, Barbas C F 3rd, Schleef R R., Recombinant rabbit Fab with binding activity to type-1 plasminogen activator inhibitor derived from a phage-display library against human alpha-granules, (1996) Gene 172(2): 295-8 and Philippa M. O'Brien, Robert Aitken, Antibody Phage Display, (2002) Methods in Molecular Biology Volume No. 178). A gene of the acquired Fab clone of the rabbit anti-CD80 antibody was incorporated into a plasmid DNA containing a gene encoding a Fc region of the rabbit antibody to acquire a plasmid DNA containing the gene of the rabbit anti-CD80 antibody. Amino acid sequences of Fd (heavy chain portion of Fab) and light chain of the rabbit anti-CD80 antibody are shown in SEQ ID NOs: 11 and 12, respectively. Base sequences encoding these amino acid sequences are shown in SEQ ID NOs: 13 and 14, respectively.
(1.2) Acquisition of Bovine Small Intestine-Derived ALP Gene A plasmid DNA containing a BIAPII gene was acquired by outsourcing gene synthesis to GenScript, based on BIA-PII amino acid sequence described in U.S. Pat. No. 6,406,899. The amino acid sequence of BIAPII and a base sequence encoding the same are shown in SEQ ID NOs: 1 and 2, respectively.
(1.3) Preparation of Fd-Linker-BIAPII Expression Vector
(i) Preparation of BIAPII Expression Vector Using a plasmid DNA containing a BIAPII gene as a template, a DNA fragment encoding BIAPII (BIAPII insert) was acquired by PCR. Using pcDNA3.4 vector as a template, linearized vector DNA was obtained by inverse PCR. PCR was performed using KOD Plus neo (Toyobo Co., Ltd.) as described in the attached document. Base sequences of primers used for PCR were as follows.

```
Primer set for vector
Forward:
                                  (SEQ ID NO: 15)
5'-TGATAAAAGGGTTCGATCCCTACC-3'

Reverse:
                                  (SEQ ID NO: 16)
5'-GCAGTGCACGGTGGCGCAGTACACC-3'

Primer set for BIAPII insert
Forward:
                                  (SEQ ID NO: 17)
5'-GCCACCGTGCACTGCTTAATTCCGGCAGAAGAAGAAACC-3'
```

-continued

Reverse:
(SEQ ID NO: 18)
5'-CGAACCCTTTTATCACGCAGGTGCAGGCAAGTTACAATC-3'

Using In-Fusion (registered trademark) HD Cloning Kit (Takara Bio Inc.), the BIAPII insert was linked to the linearized vector DNA of pcDNA3.4 to obtain a BIAPII expression vector. An In-Fusion reaction was performed according to the attached document of the kit.

(ii) Insertion of Fd Gene into BIAPII Expression Vector

Using the plasmid DNA containing the gene of the rabbit anti-CD80 antibody as a template, a DNA fragment (Fd-linker insert) encoding Fd and a peptide linker was acquired by PCR. In the obtained Fd insert, a gene encoding a peptide linker was linked downstream of a gene encoding the Fd of the rabbit anti-CD80 antibody. Types of peptide linkers were GS1, GS2, GS3, EK1, EK2 and EK3 described above. Using the BIAPII expression vector as a template, linearized vector DNA containing the BIAPII gene was obtained by inverse PCR. PCR was performed using KOD Plus neo (Toyobo Co., Ltd.) as described in the attached document. Base sequences of primers used for PCR were as follows.

```
Primer set for vector
Forward GS1:
                                            (SEQ ID NO: 19)
5'-GGTGGCGGTGGATCCTTAATTCCGGCAGAAGAAGAAACC-3'

Forward GS2:
                                            (SEQ ID NO: 20)
5'-GTGGATCCGGAGGGGCGGAAGTTTAATTCCGGCAGAAGAAGAAAAC

C-3'

Forward GS3:
                                            (SEQ ID NO: 21)
5'-GGAGGGGGCGGAAGTGGCGGGGGAGGTTCATTAATTCCGGCAGAAGA

AGAAAACC-3'

Forward EK1:
                                            (SEQ ID NO: 22)
5'-GAAGCCGCTGCTAAGTTAATTCCGGCAGAAGAAGAAAACC-3'

Forward EK2:
                                            (SEQ ID NO: 23)
5'-CTGCTAAGGAGGCAGCCGCGAAATTAATTCCGGCAGAAGAAGAAAAC

C-3'

Forward EK3:
                                            (SEQ ID NO: 24)
5'-GAGGCAGCCGCGAAAGAAGCAGCGGCTAAATTAATTCCGGCAGAAGA

AGAAAACC-3'

Reverse:
                                            (SEQ ID NO: 25)
5'-GCAGTGCACGGTGGCGCAGTACACC-3'

Primer set for Fd insert
Forward:
                                            (SEQ ID NO: 26)
5'-GCCACCGTGCACTGCCAGTCGGTGGAGGAGTCCGG-3'

Reverse GS1:
                                            (SEQ ID NO: 27)
5'-GGATCCACCGCCACCCGTGGGCTTGCTGCATGTCGAGGG-3'

Reverse GS2:
                                            (SEQ ID NO: 28)
5'-CCCCCTCCGGATCCACCGCCACCCGTGGGCTTGCTGCATGTCGAGG

G-3'

Reverse GS3:
                                            (SEQ ID NO: 29)
5'-ACTTCCGCCCCCTCCGGATCCACCGCCACCCGTGGGCTTGCTGCATG

TCGAGGG-3'

Reverse EK1:
                                            (SEQ ID NO: 30)
5'-CTTAGCAGCGGCTTCCGTGGGCTTGCTGCATGTCGAGGG-3'

Reverse EK2:
                                            (SEQ ID NO: 31)
5'-GCTGCCTCCTTAGCAGCGGCTTCCGTGGGCTTGCTGCATGTCGAGG

G-3'

Reverse EK3:
                                            (SEQ ID NO: 32)
5'-TTTCGCGGCTGCCTCCTTAGCAGCGGCTTCCGTGGGCTTGCTGCATG

TCGAGGG-3'
```

Using In-Fusion (registered trademark) HD Cloning Kit (Takara Bio Inc.), the Fd insert was linked to the linearized vector DNA containing the BIAPII gene to obtain an Fd-linker-BIAPII expression vector. An In-Fusion reaction was performed according to the attached document of the kit. In this expression vector, the gene encoding a peptide linker and the BIAPII gene were linked downstream of the gene encoding the Fd of the rabbit anti-CD80 antibody. These expression vectors correspond to the expression vectors having a structure shown in Constitution Example 1-1 above.

(1.4) Preparation of Light Chain Expression Vector

Using the plasmid DNA containing the gene of the rabbit anti-CD80 antibody as a template, a DNA fragment (LC insert) encoding a light chain was acquired by PCR. Using pcDNA3.4 vector as a template, linearized vector DNA was obtained by inverse PCR. PCR was performed using KOD Plus neo (Toyobo Co., Ltd.) as described in the attached document. Base sequences of primers used for PCR were as follows.

```
Primer set for vector
Forward:
                                            (SEQ ID NO: 33)
5'-TAATCTAGATAATTAAAGGGTTCG-3'

Reverse:
                                            (SEQ ID NO: 34)
5'-GCTGCGATAGCCCGGAAACAGTACC-3'

Primer set for LC insert
Forward:
                                            (SEQ ID NO: 35)
5'-CCGGGCTATCGCAGCGAGCTCGTGATGACCCAGAC-3'

Reverse:
                                            (SEQ ID NO: 36)
5'-TAATTATCTAGATTATCAACAGTCACCCCTATTGAAGC-3'
```

Using In-Fusion (registered trademark) HD Cloning Kit (Takara Bio Inc.), the LC insert was linked to the linearized vector DNA of pcDNA3.4 to obtain a light chain expression vector. An In-Fusion reaction was performed according to the attached document of the kit.

(2) Preparation and Culture of Antibody-Producing Cell
(2.1) Transfection into Host Cell Expi293F (trademark) cells were shake-cultured (125 rpm) at 37° C. under a 5% $CO_2$ atmosphere in a medium added with a solution of zinc chloride (KISHIDA CHEMICAL Co., Ltd.) to a final concentration of 0.1 mM. 25.5 mL of cell culture ($3.0 \times 10^6$ cells/mL) was prepared according to the number of samples. An appropriate amount of Opti-MEMI (trademark) was added to a mixture of the Fd-linker-BIAPII expression vector (about 15 µg) and the light chain expression vector (about 15 µg) to make 1.5 mL, and the mixture was gently stirred to prepare a DNA solution. The ExpiFectamine 293 reagent (80 µL) and Opti-MEMI (1.5 mL) were gently stirred and allowed to stand at room temperature for 5 minutes to prepare a transfection reagent. The DNA solution and the transfection reagent were gently stirred and allowed to stand at room temperature for 20 minutes. The resulting mixture (3 mL) was added to the cell culture (25.5 mL). The mixture was shake-cultured (125 rpm) at 37° C. for 20 hours in a 5% $CO_2$ atmosphere. After 20 hours, 150 µL and 1.5 mL of ExpiFectamine (trademark) transfection enhancers 1 and 2 were added to each culture, respectively. Each mixture was shake-cultured (125 rpm) at 37° C. for 5 days in a 5% $CO_2$ atmosphere.

(2.2) Recovery and Purification of Antibody

Culture supernatant was collected 5 days after transfection. The culture supernatant contains each ALP fusion antibody secreted from transfected Expi293F (trademark) cells. The collected culture supernatant was transferred to a centrifuge tube and centrifuged (1000 g, 5 minutes, 4° C.), and the supernatant was transferred to a new centrifuge tube. The supernatant was centrifuged again (10000 g, 10 minutes, 4° C.), and the supernatant was transferred to a new centrifuge tube. The supernatant was concentrated using Amicon Ultra-4, 30k (Merck). The concentrated supernatant was purified by gel filtration using AKTA avant25 (GE Healthcare) and Superdex 200 Increase 10/300GL (GE Healthcare). For gel filtration, by setting the injection amount to 500 µL and using an ALP buffer (100 mM triethanolamine (TEA), 150 mM NaCl, 1 mM $MgCl_2$, 0.1 mM $ZnCl_2$, pH 7.0) a running buffer, separation was performed at a flow velocity of 1 mL/min. The concentration of the ALP fusion antibody purified by gel filtration was measured from absorbance at 280 nm using nanodrop-1000 (Thermo Fisher).

[Test Example 1] Antigen Detection Ability of ALP Fusion Antibody

ELISA was performed using the ALP fusion antibody of Example 1 as a detection antibody, and antigen detection ability was examined.

(1) Measurement by Chemiluminescence ELISA

Rabbit anti-CD80 antibody (IgG) was diluted with PBS to 1 µg/mL. The resulting antibody solution was added to a 96-well black plate at 100 µL/well and allowed to stand overnight at 4° C. to immobilize the antibody in the wells. After removing the antibody solution from the plate, Buffer I' (100 mM HEPES, 1% BSA, 0.05% ProClin (trademark), 1 mM $MgCl_2$, 0.1 mM $ZnCl_2$, pH 8.0) was added at 300 µL/well and allowed to stand overnight at 4° C. for blocking. After removing the solution from the plate, a human CD80/B7-1 protein (His tag) solution (0.005, 0.020, 0.078, 0.313, 1.25, 5.0 or 20 ng/mL) was added as an antigen solution at 100 µL/well. The plate was shaken at room temperature at 500 rpm for 1 hour to perform an antigen-antibody reaction. The plate was washed three times with a HISCL washing solution (Sysmex Corporation), and then each ALP fusion antibody (200 ng/mL) of Example 1 diluted with Buffer I' was added at 100 µL/well. The plate was shaken at room temperature at 500 rpm for 1 hour to perform an antigen-antibody reaction. After washing the plate with a HISCL washing solution three times, a HISCL R5 reagent (Sysmex Corporation) as a solution of a chemiluminescent substrate of ALP was added at 100 µL/well, and luminescence intensity was immediately measured with FLUOstar OPTIMA (BMG LABTECH).

(2) Results

Figure 5:
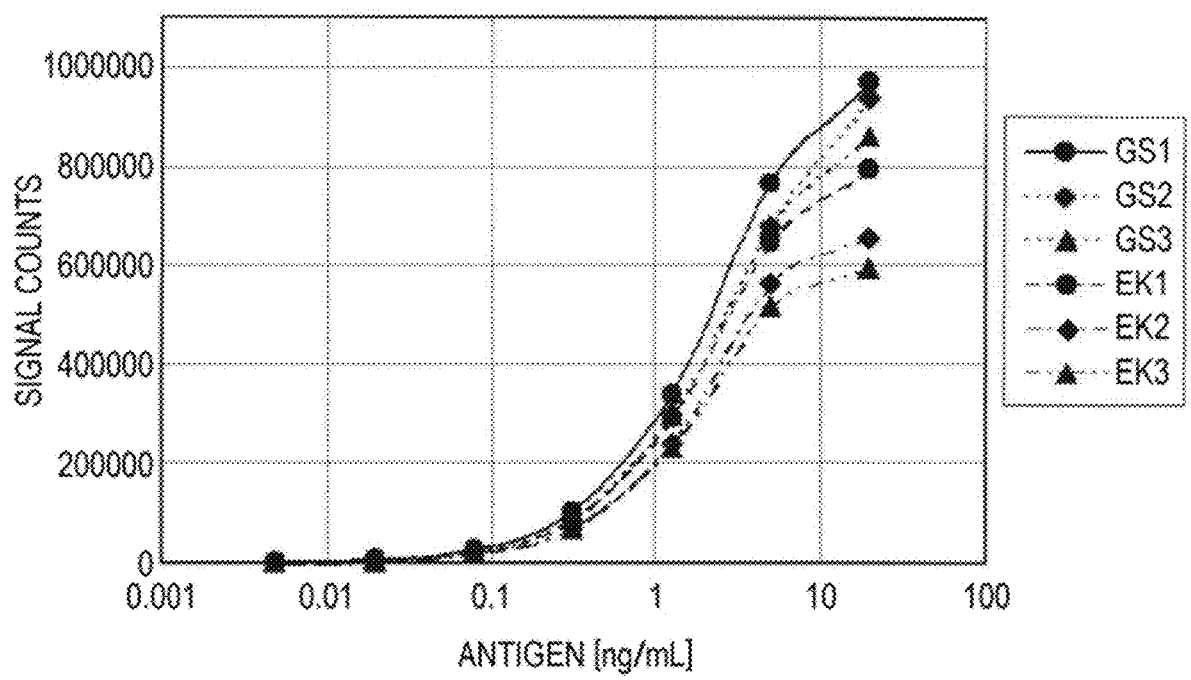
FIG. 5 is a graph showing results of measuring antigens by ELISA using ALP fusion antibodies of Example 1.

The measurement result is shown in FIG. 5. In the figure, GS1, GS2, GS3, EK1, EK2 and EK3 are types of peptide linkers in the ALP fusion antibody. As shown in the figure, the luminescence intensity increased according to antigen concentration regardless of which ALP fusion antibody was used. Therefore, it was shown that all ALP fusion antibodies had the same level of antigen detection ability.

[Test Example 2] Examination of Effects of Zinc Ion

The cells containing an expression vector obtained in Example 1 were cultured in a medium added with zinc or a medium not added with zinc under various conditions, and ALP activity of the ALP fusion antibody was measured.

(1) Culture of Antibody-Producing Cells and Recovery of Antibody (1.1) Cell Culture Using Medium not Added with Zinc The Fd-linker-BIAPII expression vector and the light chain expression vector were transfected to cells in the same manner as in Example 1 except that Expi293F (trademark) cells cultured in a normal medium not added with zinc were used. After 20 hours, the medium was replaced with a medium not added with zinc or a medium added with a zinc chloride solution (final concentration 0.1 mM). Then, ExpiFectamine (trademark) transfection enhancers 1 and 2 were added thereto, and the mixture was shake-cultured (125 rpm) at 37° C. for 5 days in a 5% $CO_2$ atmosphere. After culturing, the ALP fusion antibody (GS1 linker) was recovered and purified from culture supernatant in the same manner as in Example 1.

(1.2) Cell Culture Using Zinc-Added Medium after Expression of ALP Fusion Antibody In the same manner as in (1.1) above, transfection, medium exchange after 20 hours and culture for 5 days were performed. After 5 days, the medium was replaced with a medium not added with zinc or a medium added with a zinc chloride solution (final concentration 0.1 mM), and the cells were cultured for another 1 hour. After culturing, the ALP fusion antibody was recovered and purified from culture supernatant in the same manner as in Example 1.

(1.3) Cell Culture Using High-Concentration Zinc-Added Medium

Transfection, medium exchange after 20 hours and culture for 5 days were performed in the same manner as in Example 1 except that a medium with a zinc chloride concentration of 0.25 mM or 0.5 mM was used. After culturing, the ALP fusion antibody (GS1 linker) was recovered and purified from culture supernatant in the same manner as in Example 1. For comparison, the ALP fusion antibody (GS1 linker) was recovered and purified in the same manner as in Example 1 using a medium with a zinc chloride concentration of 0.1 mM.

(2) Measurement of ALP Activity

Figure 6A:
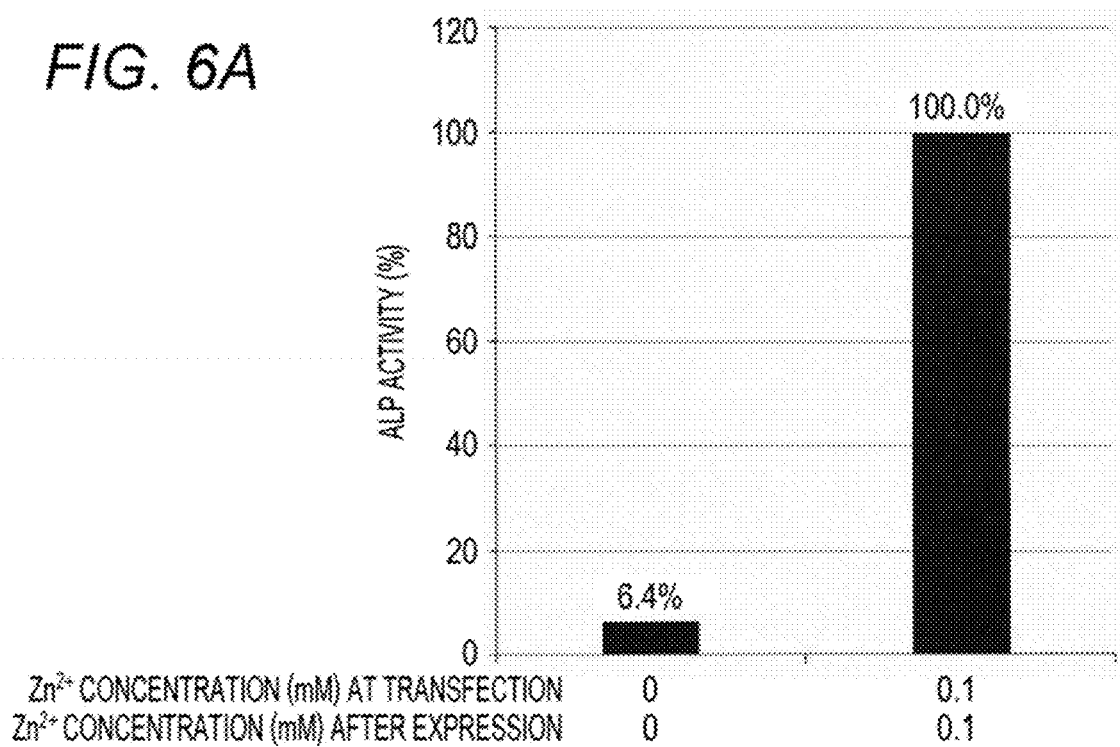
FIG. 6A is a graph showing ALP activities of ALP fusion antibodies obtained from cells cultured in media with different zinc ion addition conditions.
Figure 6B:
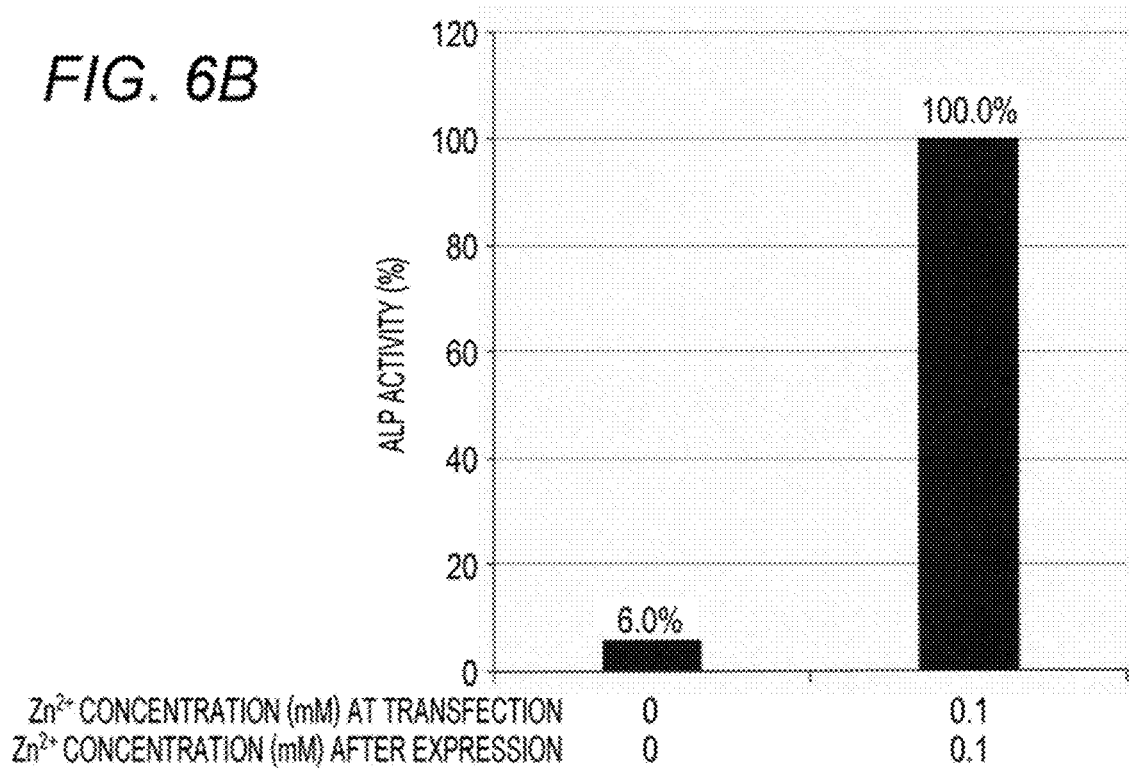
FIG. 6B is a graph showing ALP activities of ALP fusion antibodies obtained from cells cultured in media with different zinc ion addition conditions.
Figure 6C:
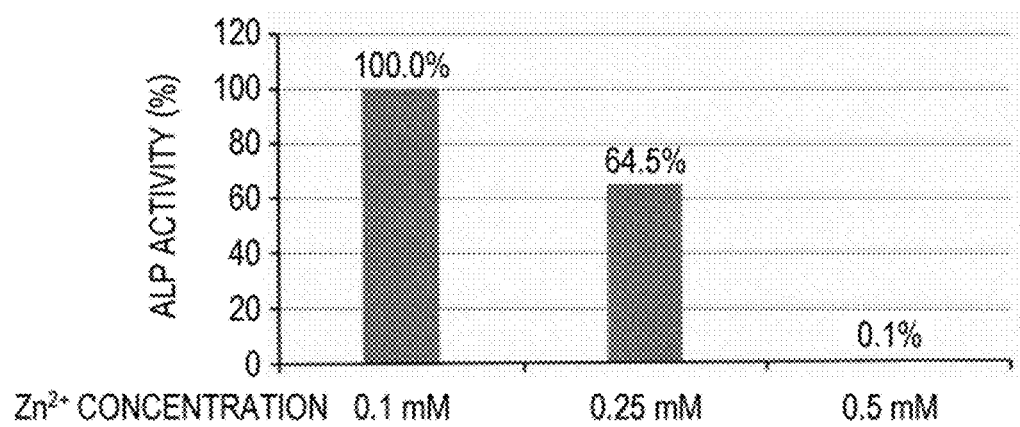
FIG. 6C is a graph showing ALP activities of ALP fusion antibodies obtained from cells cultured in media with different zinc ion concentrations.

The ALP fusion antibody was diluted with the ALP buffer. The resulting antibody solution was added to a 96-well black plate at 10 μL/well. A HISCL R5 reagent (Sysmex Corporation) was added at 100 μL/well, and luminescence intensity was immediately measured with FLUOstar OPTIMA (BMG LABTECH). The measurement results are shown in FIGS. 6A to 6C. FIGS. 6A and 6B show ALP activities of ALP fusion antibodies obtained from the cells cultured in the medium not added with zinc and the cells cultured in the zinc-added medium after expression of ALP fusion antibody when an ALP activity of an ALP fusion antibody obtained from the cells cultured in the zinc-added medium after transfection is 100%. FIG. 6C shows ALP activities of ALP fusion antibodies obtained from the cells cultured in a medium with a zinc chloride concentration of 0.25 mM or 0.5 mM when an ALP fusion antibody of an ALP fusion antibody obtained from the cells cultured in a medium having a zinc chloride concentration of 0.1 mM is 100%.

(3) Results

As shown in FIG. 6A, the ALP activity was significantly low in the ALP fusion antibody obtained from the cells cultured in the medium not added with zinc. From this result, it was shown that it is necessary to add zinc to the medium in order to exert the ALP activity of the ALP fusion antibody. As shown in FIG. 6B, the ALP activity was also significantly low in the ALP fusion antibody obtained from the cells cultured in the zinc-added medium after expression of ALP fusion antibody. From this result, it was shown that the ALP activity of the ALP fusion antibody does not increase even if zinc is added to the medium at the time when the ALP fusion antibody is considered to be expressed and it is necessary to add zinc from the time of transfection.

As shown in FIG. 6C, a sufficient ALP activity was observed even when a medium containing 0.25 mM zinc chloride was used. When a medium containing 0.5 mM zinc chloride was used, ALP activity could not be measured because the cells were dead.

[Test Example 3] Homogeneity of ALP Fusion Antibody of Example 1

Homogeneity of antibody molecules was compared between the ALP fusion antibody of Example 1 and the ALP-labeled antibody obtained by chemical modification method.

(1) Preparation of ALP-Labeled Antibody

A rabbit anti-CD80 antibody was obtained using the plasmid DNA containing the gene of the rabbit anti-CD80 antibody obtained in Example 1. From the obtained antibody, Fab was obtained by a conventional method. The obtained Fab was bound to bovine small intestine-derived ALP (ALP55, Oriental Yeast Co., ltd.) or recombinant ALP (rALP, Roche) using a crosslinking agent to obtain an ALP-labeled antibody.

(2) Size Exclusion Column Chromatography (SEC) and SDS-PAGE

The ALP fusion antibody (GS1 linker) and ALP-labeled antibody of Example 1 were separated by gel filtration using KTA avant 25 (GE Healthcare) and Superdex 200 Increase 10/300GL (GE Healthcare), respectively. Gel filtration was performed in the same manner as in Example 1. Each fraction of the ALP fusion antibody and the ALP-labeled antibody separated by gel filtration was analyzed by SDS-PAGE under non-reducing conditions.

(3) Results

Figure 7A:
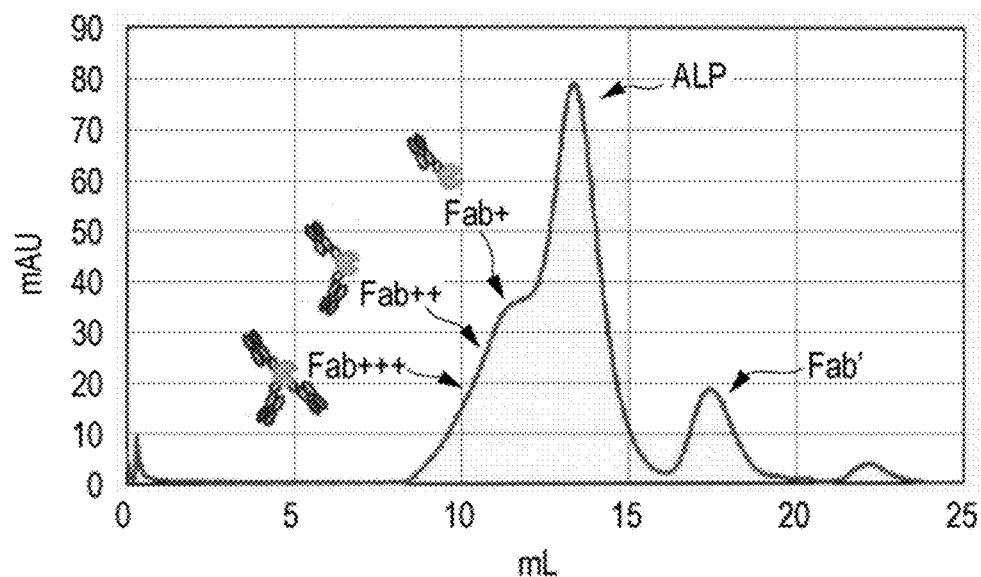
FIG. 7A is an elution curve when ALP-labeled antibodies obtained by chemical modification method was gel-filtered.
Figure 7B:
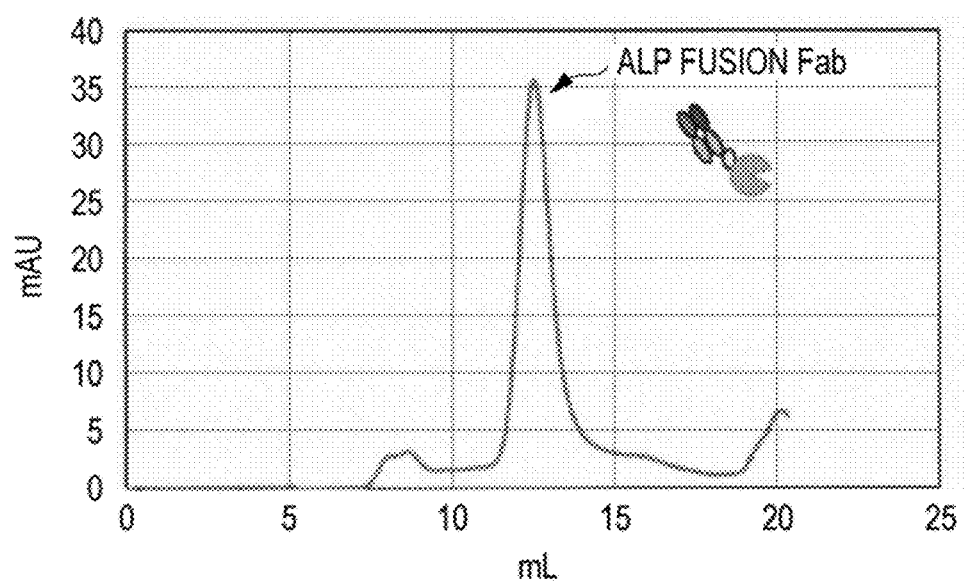
FIG. 7B is an elution curve when the ALP fusion antibody of the present embodiment was gel-filtered.
Figure 8A:
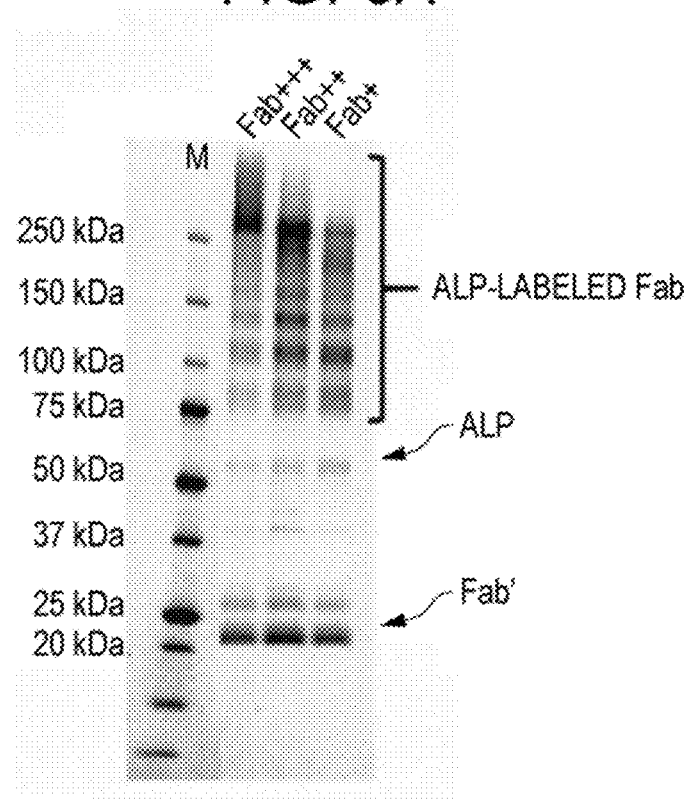
FIG. 8A is a gel when separating the ALP-labeled antibodies obtained by chemical modification method by SDS-PAGE.
Figure 8B:
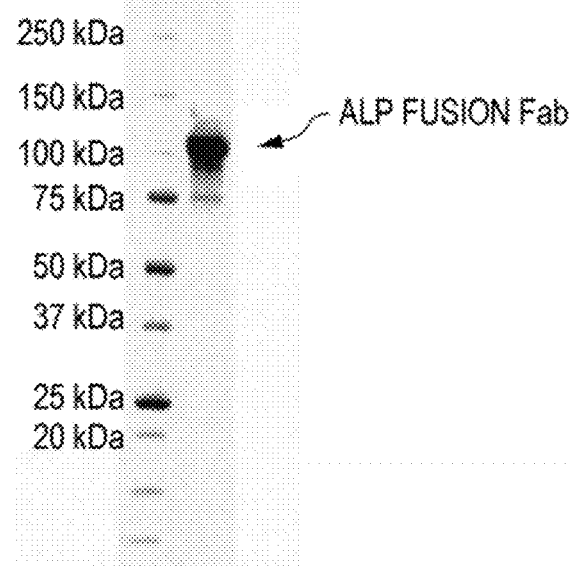
FIG. 8B is a gel when separating the ALP fusion antibody of the present embodiment by SDS-PAGE.

Elution curves of gel filtration are shown in FIGS. 7A and 7B. Results of SDS-PAGE are shown in FIGS. 8A and 8B. In the figures, "Fab+" refers to a labeled antibody in which one molecule of ALP and one molecule of Fab are bound, "Fab++" refers to a labeled antibody in which one molecule of ALP and two molecules of Fab are bound, and "Fab+++" refers to a labeled antibody in which one molecule of ALP and three molecules of Fab are bound. With reference to FIG. 7A, in gel filtration, Fab+++ was eluted in a fraction of 10 mL to 10.5 mL, Fab++ was eluted in a fraction of 11 mL to 11.5 mL, and Fab+ was eluted in a fraction of 12 mL to 12.5 mL. With reference to FIG. 7B, in gel filtration, the ALP fusion antibody was eluted in a fraction of 12 mL to 12.5 mL. As shown in FIG. 7A, it was found that the ALP-labeled antibody obtained by chemical modification method was a mixture of labeled antibodies with various molecular weights, unmodified ALP and Fab'. FIG. 8A also showed that the ALP-labeled antibody obtained by chemical modification method was not uniform. On the other hand, as shown in FIGS. 7B and 8B, a sharp single peak was observed in the elution curve of the ALP fusion antibody. Therefore, it was found that the ALP fusion antibody of the present embodiment is a homogeneous group of molecules.

[Test Example 4] Performance of Reagent Containing ALP Fusion Antibody of Example 1

A reagent for a fully automatic immunoassay device was prepared using the ALP fusion antibody of Example 1, and performance of this reagent was examined. For comparison, reagents using each fraction of the ALP-labeled antibody isolated in Test Example 3 were also examined.

(1) Preparation of Reagents

An R1 reagent (capture antibody reagent) was prepared by labeling a rabbit anti-CD80 antibody (semi-IgG) with biotin by a conventional method and dissolving it in a buffer for R1 reagent (50 mM HEPES, 150 mM NaCl, 1% BSA, pH 7.4). As an R2 reagent (solid phase), a HISCL (registered trademark) R2 reagent (Sysmex Corporation) containing streptavidin-coupled magnetic particles was used. An R3 reagent (detection antibody reagent) was prepared by dissolving the ALP fusion antibody (GS1 linker) of Example 1 in a buffer for R3 reagent (50 mM HEPES, 1 mM $MgCl_2$, 0.1 mM $ZnCl_2$, 1% BSA, pH 7.3). The concentration of the ALP fusion antibody in the R3 reagent was 200 ng/mL. For comparison, R3 reagents containing each fraction of the ALP-labeled antibody (Fab+, Fab++ or Fab+++) were prepared in the same manner. The concentration of the ALP-labeled antibody in the R3 reagent was adjusted so as to be approximately equal to the ALP activity of the R3 reagent containing the ALP fusion antibody. As an R4 reagent (measurement buffer), a HISCL R4 reagent (Sysmex Corporation) was used. As an R5 reagent (substrate solution), a HISCL R5 reagent (Sysmex Corporation) was used. An antigen solution was prepared by serially diluting human CD80/B7-1 protein (His tag) with Buffer I'. A HISCL washing solution (Sysmex Corporation) was used as a washing solution for magnetic particles.

(2) Measurement

A measurement was performed using the reagents with a fully automatic immunoassay device HISCL-800 (manufactured by Sysmex Corporation). This measurement is based on sandwich ELISA on magnetic particles. Specific operations are as follows. The antigen solution (20 μL) was added to the R1 reagent (50 μL) and mixed, and then the R2 reagent (30 μL) was added and mixed. The magnetic particles in the obtained mixed solution were magnetically collected to remove the supernatant, and a HISCL washing solution (300 μL) was added to wash the magnetic particles. The supernatant was removed, and the R3 reagent (100 μL) was added to the magnetic particles and mixed. The magnetic particles in the obtained mixed solution were magnetically collected to remove the supernatant, and a HISCL washing solution (300 μL) was added to wash the magnetic particles. The supernatant was removed, and the R4 reagent (50 μL) and the R5 reagent (100 μL) were added to the magnetic particles and thoroughly mixed, and chemiluminescence intensity was measured. In order to examine a background of the measurement, a measurement was performed in the same manner as above except that Buffer I' containing no antigen was used instead of the antigen solution. SN ratios of measurement were calculated from the measured values of each antigen solution and the backgrounds.

(3) Results

Figure 9A:
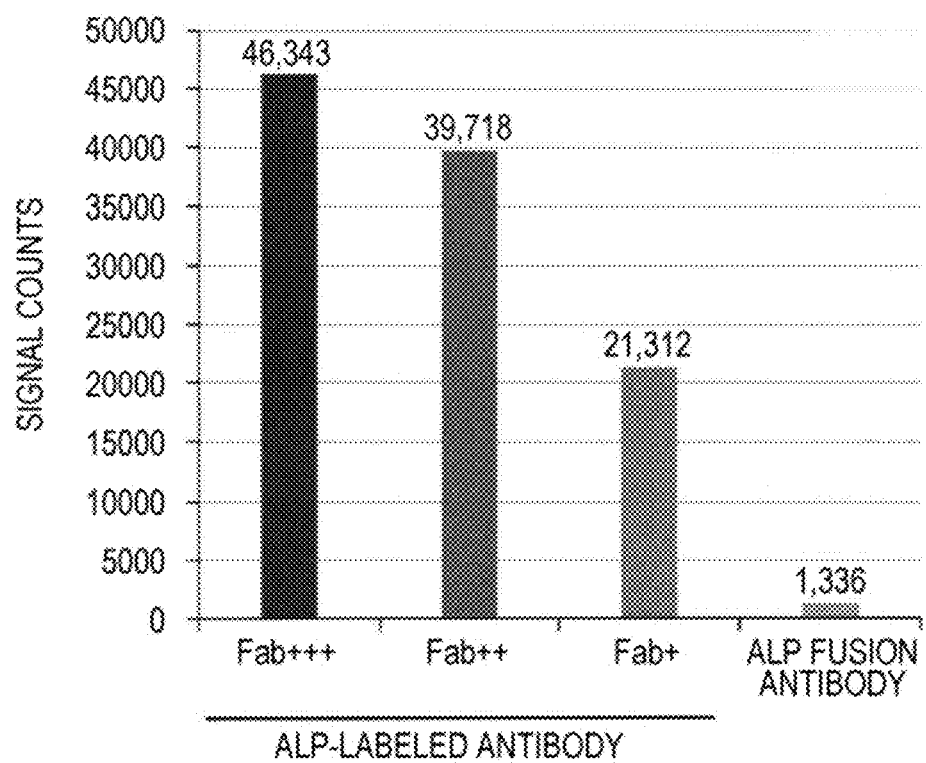
FIG. 9A is a graph showing backgrounds of immunoassay using the ALP-labeled antibodies and the ALP fusion antibody of the present embodiment.
Figure 9B:
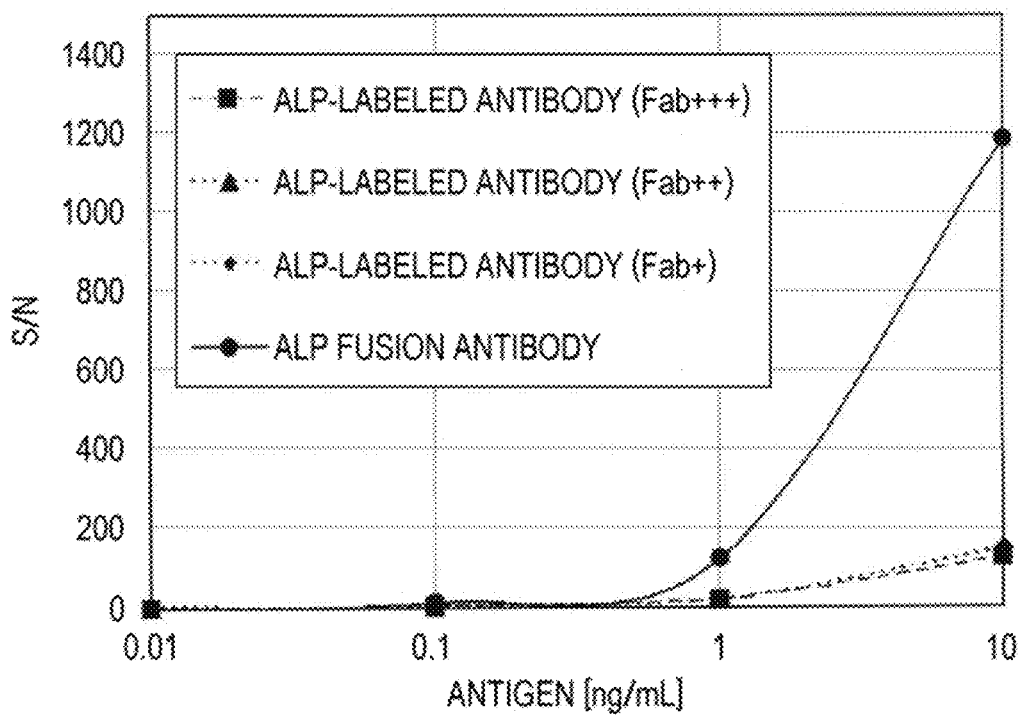
FIG. 9B is a graph showing SN ratios of immunoassay using the ALP-labeled antibodies and the ALP fusion antibody of the present embodiment.

The measurement results are shown in FIGS. 9A and 9B. As shown in FIG. 9A, the background was significantly lower when the ALP fusion antibody was used as the detection antibody than when the ALP-labeled antibody was used. As shown in FIG. 9B, the SN ratio was significantly higher when the ALP fusion antibody was used as the detection antibody than when the ALP-labeled antibody was used. From these results, it was found that the antigen can be detected with higher sensitivity by using the detection antibody reagent containing the ALP fusion antibody than by using the detection antibody reagent containing the ALP-labeled antibody obtained by chemical modification method.

[Example 2] Preparation of Bovine Small Intestine-Derived ALP Fusion Antibody (2)

As an ALP fusion antibody having an antibody portion different from that of the ALP fusion antibody of Example 1, a fusion protein in which Fab of a mouse anti-human IgG antibody and the ALP subunit were bound was prepared. This corresponds to the ALP fusion antibody having a structure shown in Antibody Example 1-1 above.

(1) Preparation of Expression Vector

Lymphocytes were acquired from peripheral blood of a mouse immunized with human IgG, and mRNA was extracted from the lymphocytes to synthesize cDNA. Using the obtained cDNA, a plasmid DNA containing a gene of the mouse anti-human IgG antibody was acquired in the same manner as in Example 1. Using the plasmid DNA containing this antibody gene and the BIAPII expression vector of Example 1, an Fd-linker-BIAPII expression vector was obtained in the same manner as in Example 1. In the obtained expression vector, the gene encoding the peptide linker GS1, GS3, EK1 or EK3 and the BIAPII gene were linked downstream of a gene encoding Fd of the mouse anti-human IgG antibody. Using the plasmid DNA containing a gene of the mouse anti-human IgG antibody, a light chain expression vector was obtained in the same manner as in Example 1.

(2) Preparation and Culture of Antibody-Producing Cell

In the same manner as in Example 1, the above expression vector was transfected into Expi293F (trademark) cells cultured in a medium added with a zinc chloride solution. Culture supernatant was collected 5 days after transfection, and the ALP fusion antibody was concentrated and purified in the same manner as in Example 1.

[Test Example 5] Quality of Reagent Containing ALP Fusion Antibody of Example 2

Homogeneity of molecules was compared between the ALP fusion antibody obtained in Example 2 and the ALP-labeled antibody obtained by chemical modification method. A reagent for a fully automatic immunoassay device was prepared using the ALP fusion antibody obtained in Example 2, and performance and storage stability of this reagent were examined. For comparison, reagents using the ALP-labeled antibody were also examined.

(1) Preparation of ALP-Labeled Antibody and Confirmation of Homogeneity of Antibody Molecule In the same manner as in Test Example 3, Fab of the mouse anti-human IgG antibody was bound to ALP55 (Oriental Yeast Co., ltd.) or rALP (Roche) to obtain an ALP-labeled antibody. Each of the ALP fusion antibody and the ALP-labeled antibody obtained in Example 2 was separated by gel filtration in the same manner as in Test Example 3. Each fraction of the ALP fusion antibody and the ALP-labeled antibody separated by gel filtration was analyzed by SDS-PAGE under non-reducing conditions. As for the results of gel filtration and SDS-PAGE, similar to the results of Test Example 3, the ALP-labeled antibody obtained by chemical modification method was a mixture of labeled antibodies with various molecular weights, unmodified ALP and Fab'. On the other hand, the ALP fusion antibody was a homogeneous group of molecules.

(2) Preparation and Measurement of Reagents

Figure 10:
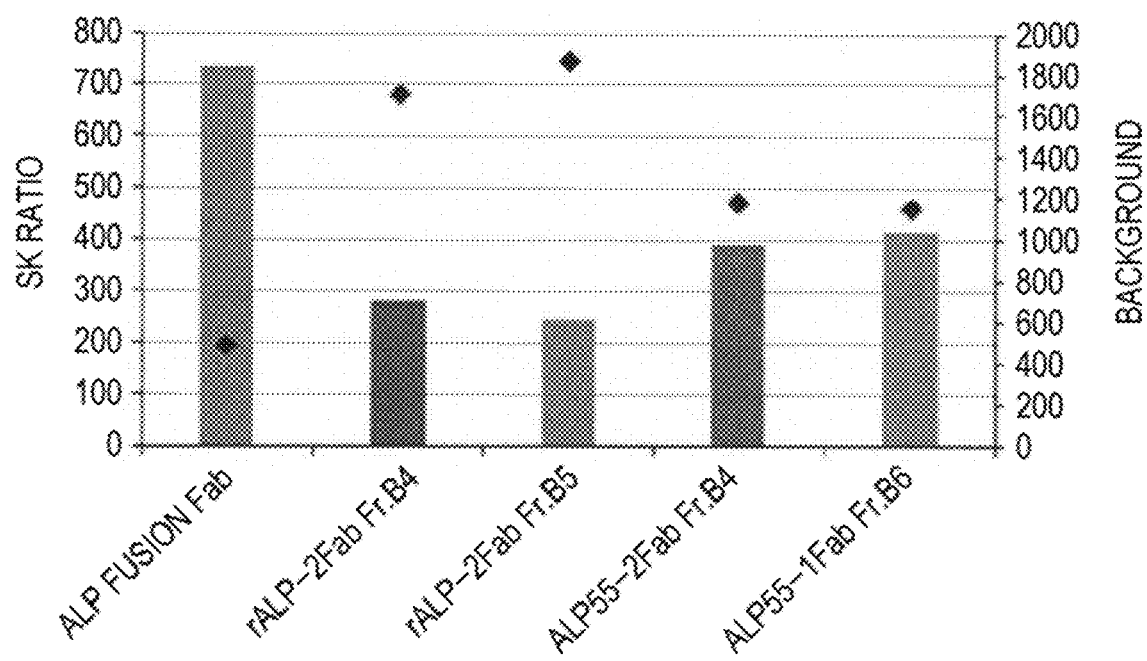
FIG. 10 is a graph showing backgrounds and SN ratios of immunoassay using the ALP-labeled antibodies and the ALP fusion antibody of the present embodiment.

In the same manner as in Test Example 4, an R1 reagent containing a biotin-labeled mouse anti-human IgG antibody (semi-IgG) and an R3 reagent containing the ALP fusion antibody obtained in Example 2 were prepared. For comparison, R3 reagents containing the ALP-labeled antibody of the fraction obtained by gel filtration were prepared in the same manner. As the fractions of ALP-labeled antibody, fractions (rALP-2Fab Fr.B4, rALP-2Fab Fr.B5 and ALP55-2Fab Fr.B4) containing a labeled antibody in which one molecule of ALP and two molecules of Fab are bound, and a fraction (ALP55-1Fab Fr B6) containing a labeled antibody in which one molecule of ALP and one molecule of Fab are bound were used. The antibody concentration in each R3 reagent was adjusted based on the ALP activity of each antibody. An antigen solution was prepared by diluting human IgG antibody with Buffer I'. The R2 reagent, R4 reagent, R5 reagent and washing solution were the same as those in Example 4. Measurements were performed with HISCL-800 (manufactured by Sysmex Corporation) using these reagents, and backgrounds and SN ratios of measurement were calculated. The measurement result is shown in FIG. 10. In FIG. 10, a point indicated by ♦ indicates the background value, and a bar in the graph indicates the SN ratio.

(3) Examination of Storage Stability of Reagents

Using the R3 reagent stored at 4° C. and the R3 reagent stored at 40° C. for 1 week, Buffer I' containing no antigen solution and antigen was measured with HISCL-800 (manufactured by Sysmex Corporation), and the measured values were compared. The results are shown in Table 1. In the table, "NC" indicates Buffer I' containing no antigen, PC indicates an antigen solution, "Counts" indicates a measured value, and "vs. 4° C." indicates a ratio of the measured value obtained using the R3 reagent stored at 40° C. for 1 week to the measured value obtained using the R3 reagent stored at 4° C.

TABLE 1

| R3 Reagent | Antibody Concentration (U/mL) | Activity (4° C. storage) | | | | | Activity (40° C., 1 week) | | | |
|---|---|---|---|---|---|---|---|---|---|---|
| | | NC | | PC | | | NC | | PC | |
| | | Counts | CV | Counts | CV | S/N | Counts | vs. 4° C. | Counts | vs. 4° C. |
| ALP Fusion antibody (GS1) | 0.051 | 487 | 3.1% | 358746 | 0.8% | 737 | 467 | 96% | 320009.7 | 89% |
| ALP Fusion antibody (GS3) | 0.051 | 494 | 1.6% | 364493 | 1.3% | 737 | 504 | 102% | 330667.7 | 91% |
| ALP Fusion antibody (EK1) | 0.052 | 500 | 1.1% | 463350 | 2.4% | 927 | 517 | 103% | 421357.3 | 91% |
| ALP Fusion antibody (EK3) | 0.055 | 699 | 3.3% | 464567 | 2.0% | 665 | 716 | 102% | 435997.7 | 94% |
| rALP-2Fab Fr.B4 | 0.086 | 1699 | 4.0% | 476857 | 1.5% | 281 | 1310 | 77% | 368836.0 | 77% |
| rALP-2Fab Fr.B5 | 0.085 | 1866 | 0.9% | 454067 | 0.9% | 243 | 1403 | 75% | 348915.0 | 77% |
| ALP55-2Fab Fr.B4 | 0.129 | 1181 | 2.9% | 464031 | 1.6% | 393 | 1169 | 99% | 379968.7 | 82% |
| ALP55-1Fab Fr.B6 | 0.172 | 1152 | 4.4% | 479008 | 3.2% | 416 | 1127 | 98% | 393871.3 | 82% |

(4) Results

As shown in FIG. 10, the background was significantly lower when the ALP fusion antibody was used than when the ALP-labeled antibody was used. The SN ratio was significantly higher when the ALP fusion antibody was used than when the ALP-labeled antibody was used. As shown in Table 1, it was found that when each R3 reagent was stored at 40° C. for 1 week, PC measured values with the R3 reagent containing the ALP fusion antibody did not decrease much as compared to PC measured values with the R3 reagent containing the ALP-labeled antibody. Therefore, it was shown that the reagent containing the ALP fusion antibody has higher storage stability than the reagent containing the ALP-labeled antibody.

[Example 3] Preparation of Bovine Small Intestine-Derived ALP Fusion Antibody (3)

Using the plasmid DNA containing the antibody gene obtained in Example 2 and the BIAPII expression vector, expression vectors having a structure shown in any of Constitution Examples 1-2, 1-3, 2-1 and 2-2 were shown were prepared by the same method as in Example 1. Using these expression vectors, the ALP fusion antibodies shown in Antibody Examples 1-2, 1-3, 2-1 and 2-2 were prepared.

(1) Preparation of Expression Vector and Acquisition of Antibody (1.1) ALP Fusion Antibody of Antibody Example 1-2

Using the plasmid DNA containing the antibody gene obtained in Example 2 as a template, a DNA fragment encoding a light chain and a peptide linker was acquired. The obtained DNA fragment was linked to a linearized BIAPII expression vector DNA to prepare an LC-linker-BIAPII expression vector. In this expression vector, the gene encoding a peptide linker and the BIAPII gene were linked downstream of the gene encoding a light chain. Using the plasmid DNA containing the antibody gene as a template, a DNA fragment encoding Fd was acquired, and an expression vector containing the gene encoding Fd (Fd expression vector) was prepared in the same manner as in Example 1. These expression vectors were transfected into Expi293F (trademark) cells to obtain the ALP fusion antibody of Antibody Example 1-2.

(1.2) ALP Fusion Antibody of Antibody Example 1-3

Using the plasmid DNA containing the antibody gene obtained in Example 2 as a template, a DNA fragment encoding Fd was acquired. The obtained DNA fragment was linked to a linearized BIAPII expression vector DNA to prepare an Fd-BIAPII expression vector. In this expression vector, the BIAPII gene was linked downstream of the gene encoding Fd. This expression vector and the light chain expression vector obtained in Example 2 were transfected into Expi293F (trademark) cells to obtain the ALP fusion antibody of Antibody Example 1-3.

(1.3) ALP Fusion Antibody of Antibody Example 2-1

Using the plasmid DNA containing the antibody gene obtained in Example 2 as a template, a DNA fragment encoding a peptide linker and Fd was acquired. The obtained DNA fragment was linked to a linearized BIAPII expression vector DNA to prepare a BIAPII-linker-Fd expression vector. In this expression vector, the gene encoding a peptide linker and the gene encoding Fd were linked downstream of the BIAPII gene. This expression vector and the light chain expression vector obtained in Example 2 were transfected into Expi293F (trademark) cells to obtain the ALP fusion antibody of Antibody Example 2-1.

(1.4) ALP Fusion Antibody of Antibody Example 2-2

Using the plasmid DNA containing the antibody gene obtained in Example 2 as a template, a DNA fragment encoding a peptide linker and a light chain was acquired. The obtained DNA fragment was linked to a linearized BIAPII expression vector DNA to prepare a BIAPII-linker-LC expression vector. In this expression vector, the gene encoding a peptide linker and the gene encoding a light chain were linked downstream of the BIAPII gene. This expression vector and the Fd expression vector were transfected into Expi293F (trademark) cells to obtain the ALP fusion antibody of Antibody Example 2-2.

(2) Examination of Homogeneity of Antibody Molecule and Performance of Reagent

Figure 11A:
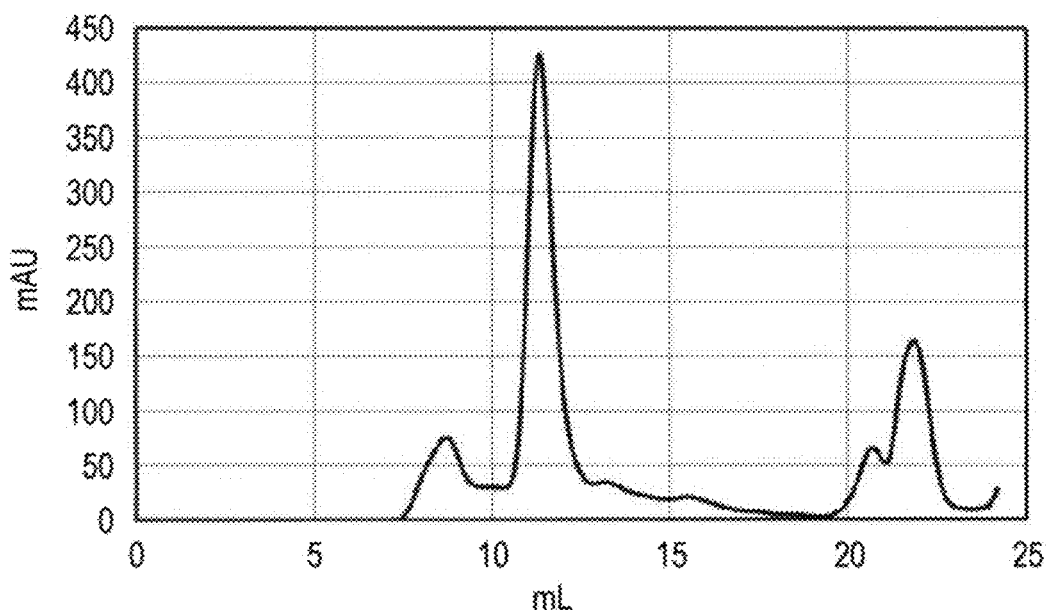
FIG. 11A is an elution curve when the ALP fusion antibody of Example 3 (Antibody Example 1-2) was gel-filtered.
Figure 11B:
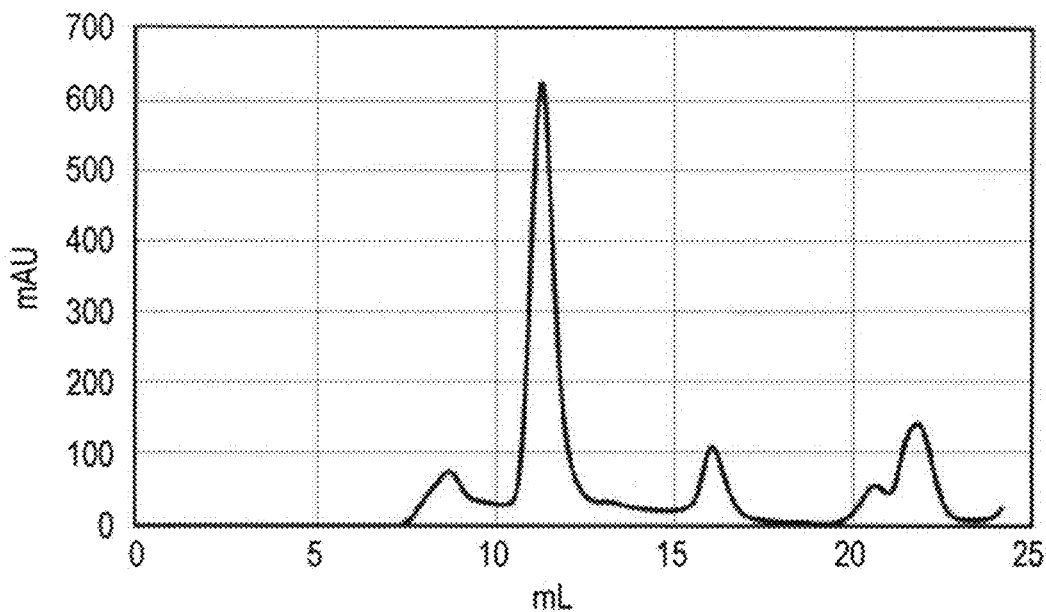
FIG. 11B is an elution curve when the ALP fusion antibody of Example 3 (Antibody Example 1-3) was gel-filtered.
Figure 11C:
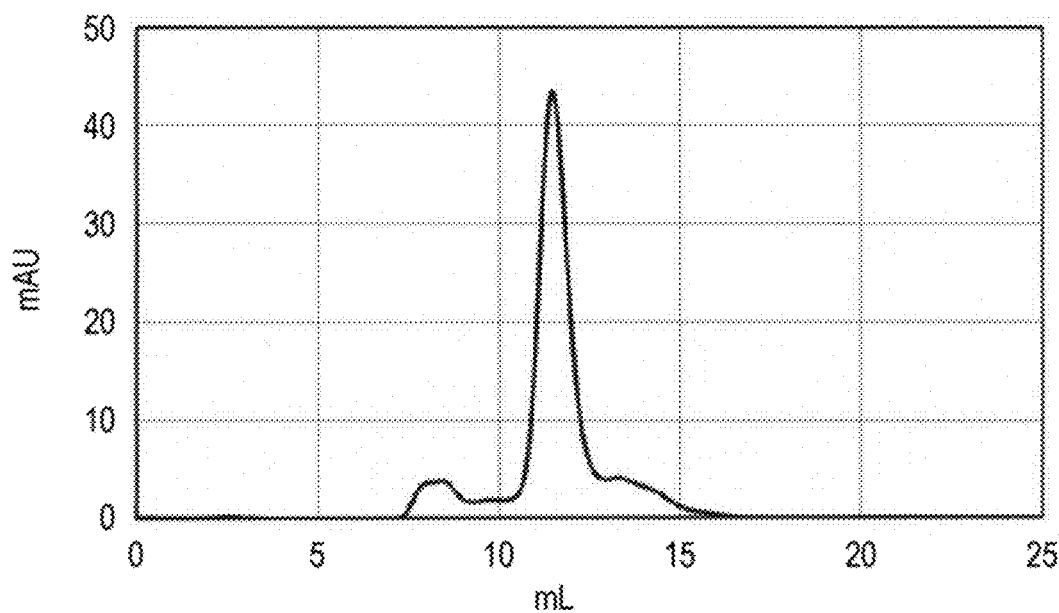
FIG. 11C is an elution curve when the ALP fusion antibody of Example 3 (Antibody Example 2-1) was gel-filtered.
Figure 11D:
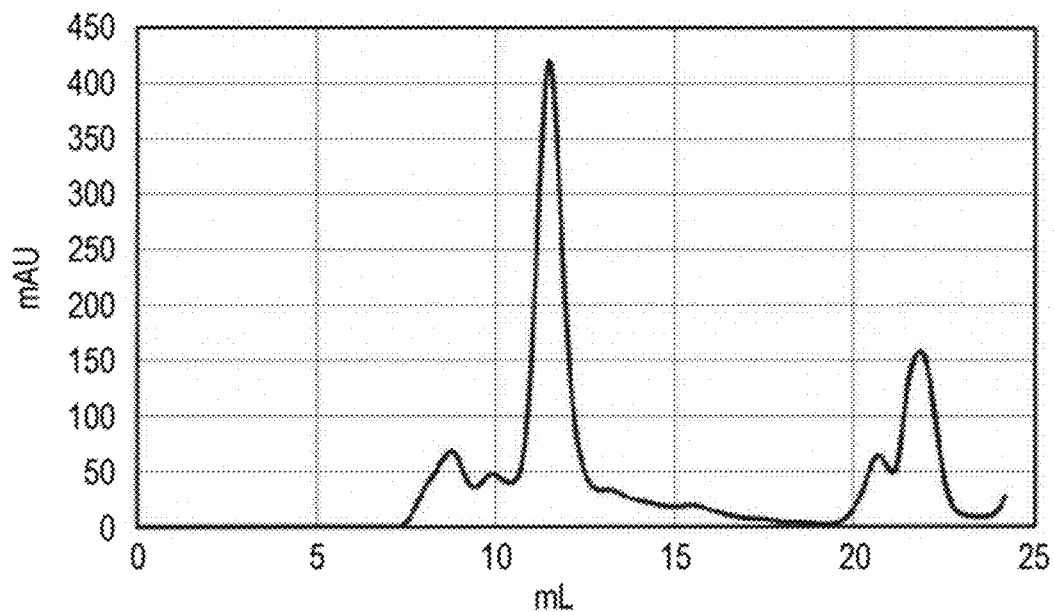
FIG. 11D is an elution curve when the ALP fusion antibody of Example 3 (Antibody Example 2-2) was gel-filtered.
Figure 11E:
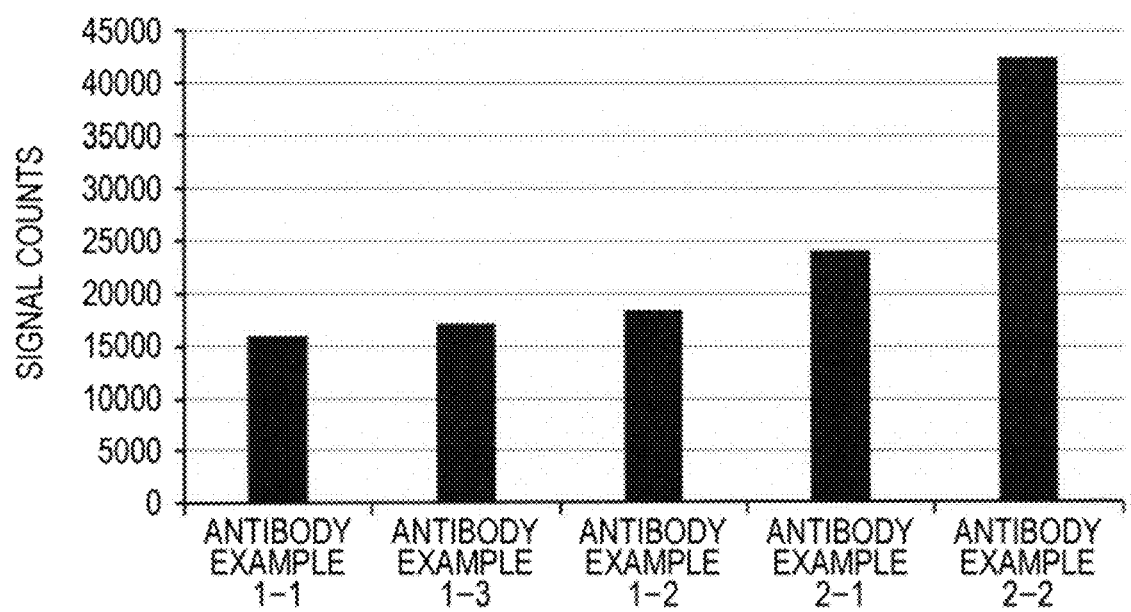
FIG. 11E is a graph showing ALP activities of the ALP fusion antibodies of Example 3.
Figure 11F:
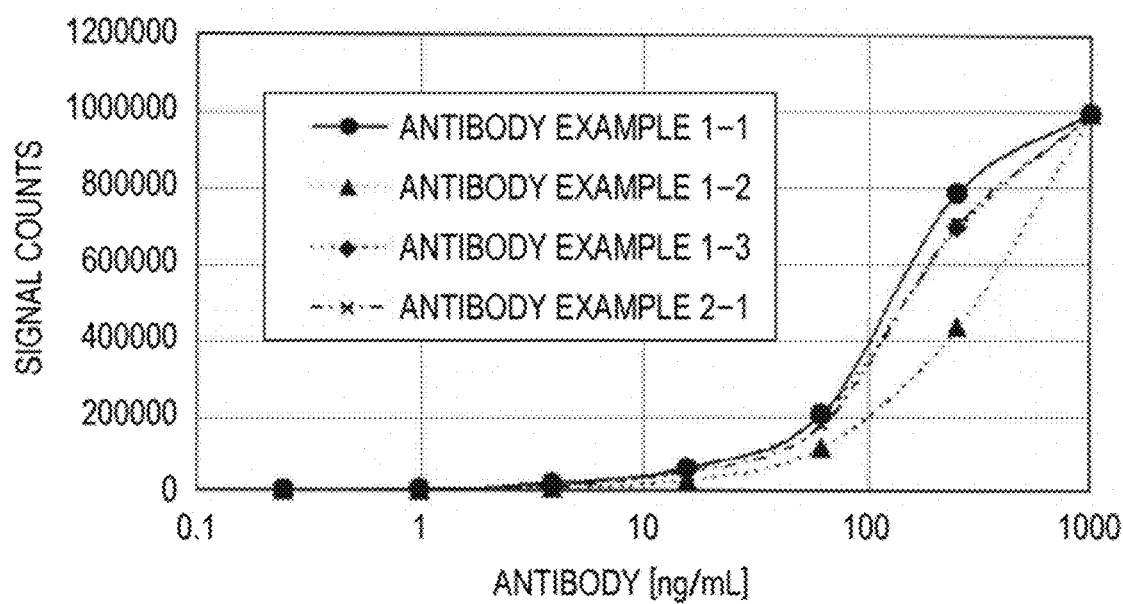
FIG. 11F is a graph showing results of measuring antigens by ELISA using the ALP fusion antibodies of Example 3.

Using each of the prepared ALP fusion antibodies, homogeneity of the antibody molecule was examined in the same manner as in Test Example 3. Results of gel filtration are shown in FIGS. 11A to 11D. ALP activity of each ALP fusion antibody was measured in the same manner as in Test Example 2. For comparison, measurements using the ALP fusion antibody of Example 1 (Antibody Example 1-1) were also performed. The results are shown in FIG. 11E. ELISA was performed in the same manner as in Test Example 1 except that the ALP fusion antibodies of Antibody Examples 1-2, 1-3 and 2-1 obtained in (1) above were used as detection antibodies instead of the ALP fusion antibody of Example 1. For comparison, measurements using the ALP fusion antibody of Example 1 (Antibody Example 1-1) were also performed. The results are shown in FIG. 11F.

With reference to FIGS. 11A to 11D, in gel filtration, the ALP fusion antibodies of Antibody Examples 1-2, 1-3, 2-1 and 2-2 were all eluted into a fraction of 11 mL to 11.5 mL. As shown in FIGS. 11A to 11D, the obtained ALP fusion antibodies were homogeneous molecular assemblies. As shown in FIG. 11E, the obtained ALP fusion antibody had ALP activity. As shown in FIG. 11F, the luminescence intensity of each ALP fusion antibody of Antibody Examples 1-2, 1-3 and 2-1 increased according to antigen concentration, similar to the ALP fusion antibody of Antibody Example 1-1. Therefore, the ALP fusion antibodies of Antibody Examples 1-2, 1-3 and 2-1 all had antigen detection ability.

[Example 4] Preparation of Bovine Small Intestine-Derived ALP Fusion Antibody (4)

Figure 12A:
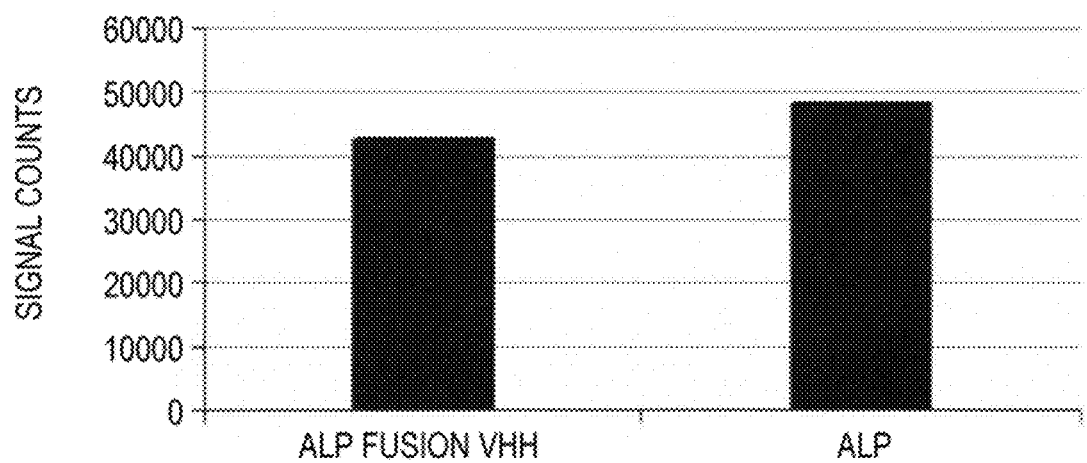
FIG. 12A is a graph showing ALP activities of the ALP fusion antibody of Example 4.
Figure 12B:
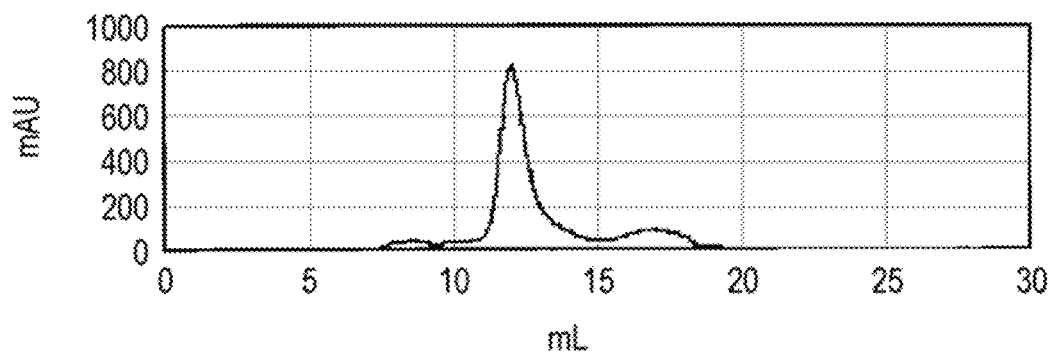
FIG. 12B is an elution curve when the ALP fusion antibody of Example 4 was gel-filtered.

A fusion protein in which VHH of an alpaca anti-CTLA-4 antibody and the ALP subunit were bound was prepared to obtain an ALP fusion antibody. This corresponds to the ALP fusion antibody having a structure shown in Antibody Example 3-1 above.
(1) Preparation of Expression Vector and Acquisition of Antibody
Using a plasmid DNA containing a gene encoding VHH of the alpaca anti-CTLA-4 antibody as a template, a DNA fragment encoding VHH and a peptide linker (GS1 linker) was acquired. The obtained DNA fragment was linked to a linearized BIAPII expression vector DNA to prepare a VHH-linker-BIAPII expression vector. In this expression vector, the gene encoding a peptide linker and the BIAPII gene were linked downstream of the gene encoding VHH. The VHH-linker-BIAPII expression vector was transfected into Expi293F (trademark) cells to obtain the ALP fusion antibody of Antibody Example 3-1.
(2) Measurement of ALP Activity and Examination of Homogeneity of Antibody Molecule
ALP activity of the ALP fusion antibody was measured in the same manner as in Test Example 2. For comparison, an activity of ALP of BIAPII obtained by transfecting the BIAPII expression vector of Example 1 into Expi293F (trademark) cells was also measured. The results are shown in FIG. 12A. Homogeneity of the antibody molecule was examined by gel filtration in the same manner as in Test Example 3. An elution curve is shown in FIG. 12B. In gel filtration, the ALP-fused anti-CTLA4 antibody of Antibody Example 3-1 was eluted in a fraction of 12 mL to 12.5 mL. As shown in FIG. 12A, the obtained ALP fusion antibody had ALP activity. As shown in FIG. 12B, the obtained ALP fusion antibody was a homogeneous molecular assembly.

[Example 5] Preparation of Bovine Small Intestine-Derived ALP Fusion Antibodies (5)

Figure 13A:
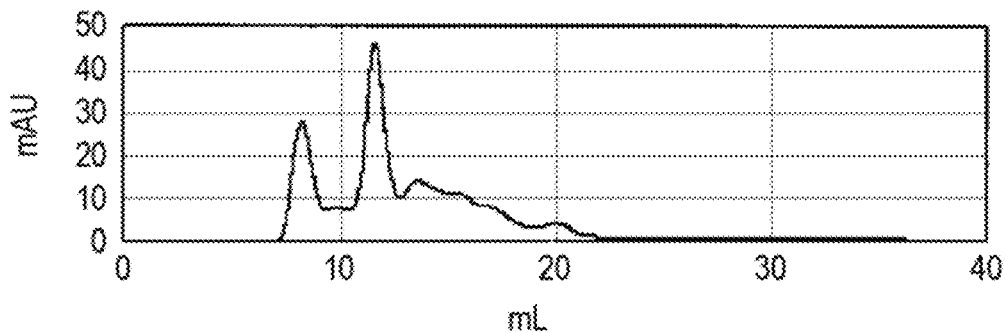
FIG. 13A is an elution curve when the ALP fusion antibody (Fab of rabbit anti-PD-1 antibody) of Example 5 was gel-filtered.
Figure 13B:
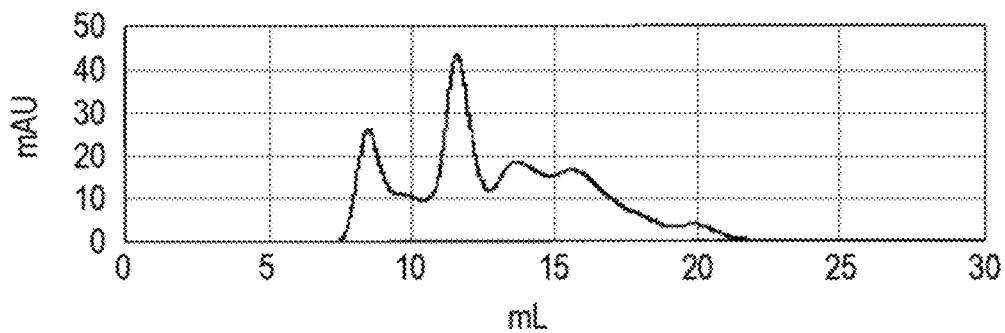
FIG. 13B is an elution curve when the ALP fusion antibody (Fab of rabbit anti-PD-L1 antibody) of Example 5 was gel-filtered.
Figure 13C:
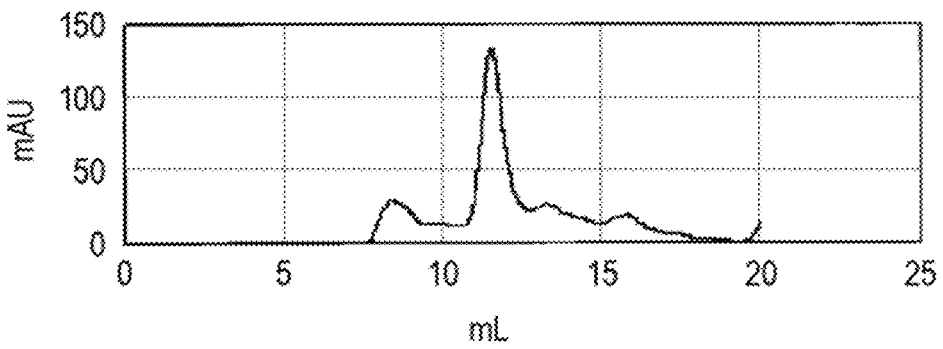
FIG. 13C is an elution curve when the ALP fusion antibody (Fab of mouse anti-VEGF antibody) of Example 5 was gel-filtered.
Figure 14A:
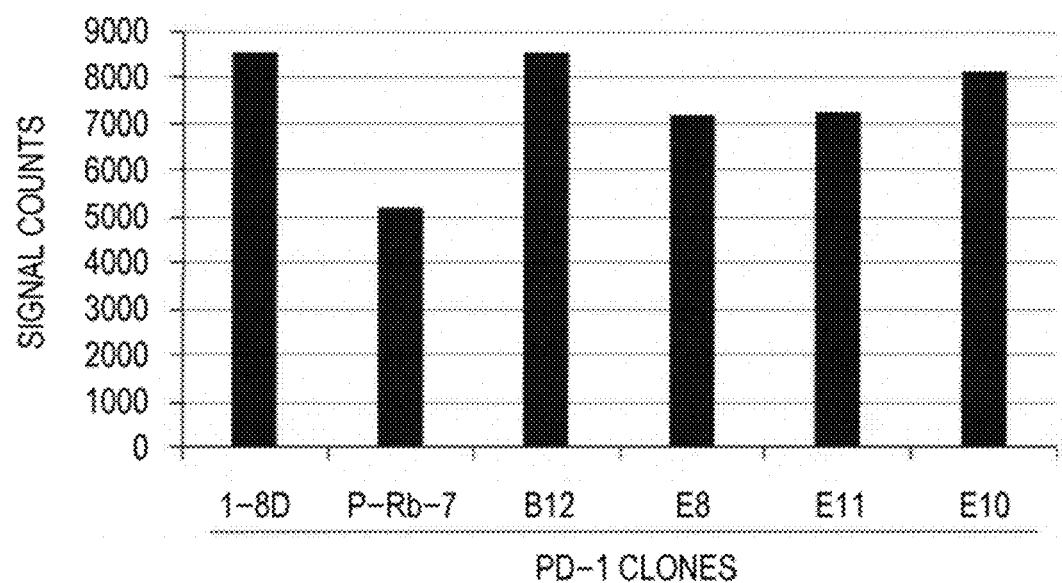
FIG. 14A is a graph showing ALP activities of the ALP fusion antibodies (Fab of rabbit anti-PD-1 antibodies) of Example 5.
Figure 14B:
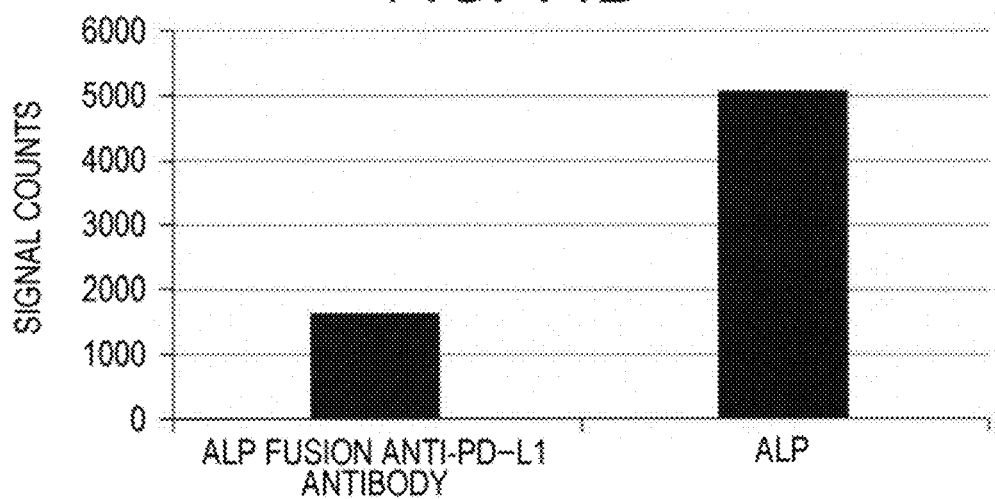
FIG. 14B is a graph showing ALP activity of the ALP fusion antibody (Fab of rabbit anti-PD-L1 antibodies) of Example 5.

As ALP fusion antibodies having an antibody portion different from that of the ALP fusion antibody of Example 1, fusion proteins in which Fab of rabbit anti-PD-1 antibody, rabbit anti-PD-L1 antibody or mouse anti-VEGF antibody and the ALP subunit were bound were prepared. This corresponds to the ALP fusion antibody having a structure shown in Antibody Example 1-1 above.
(1) Preparation of Expression Vector
An Fd-linker-BIAPII expression vector containing a gene encoding Fd of a rabbit anti-PD-1 antibody or a rabbit anti-PD-L1 antibody and a light chain expression vector containing a gene encoding a light chain of the antibody were obtained in the same manner as in Example 1, except that PD-1 or PD-L1 was used as an immunogen. As for an antibody gene of the anti-PD-1 antibody, since multiple clones were obtained, ALP fusion antibodies of each clone were prepared. An Fd-linker-BIAPII expression vector containing a gene encoding Fd of a mouse anti-VEGF antibody and a light chain expression vector containing a gene encoding a light chain of the antibody were obtained in the same manner as in Example 2, except that VEGF was used as an immunogen. The peptide linker was a GS1 linker.
(2) Examination of Homogeneity of Antibody Molecule and Measurement of ALP Activity
Homogeneity of molecules of each ALP fusion antibody were examined by gel filtration in the same manner as in Test Example 3. Elution curves are shown in FIGS. 13A to 13C. Using an ALP-fused anti-PD-1 antibody or an ALP-fused anti-PD-L1 antibody, ALP activities measured in the same manner as in Test Example 2. The results are shown in FIGS. 14A and 14B. With reference to FIGS. 13A to 13C, in gel filtration, the ALP-fused anti-PD1 antibody, the ALP-fused anti-PD-L1 antibody and the ALP-fused anti-VEGF antibody were all eluted into a fraction of 11.5 mL to 12 mL. As shown in FIGS. 13A to 13C, the obtained ALP fusion antibodies were homogeneous molecular assemblies. As shown in FIGS. 14A and 14B, the obtained ALP fusion antibodies had ALP activity.

[Example 6] Preparation of *Shewanella* Bacterium-Derived ALP Fusion Antibody

Figure 15A:
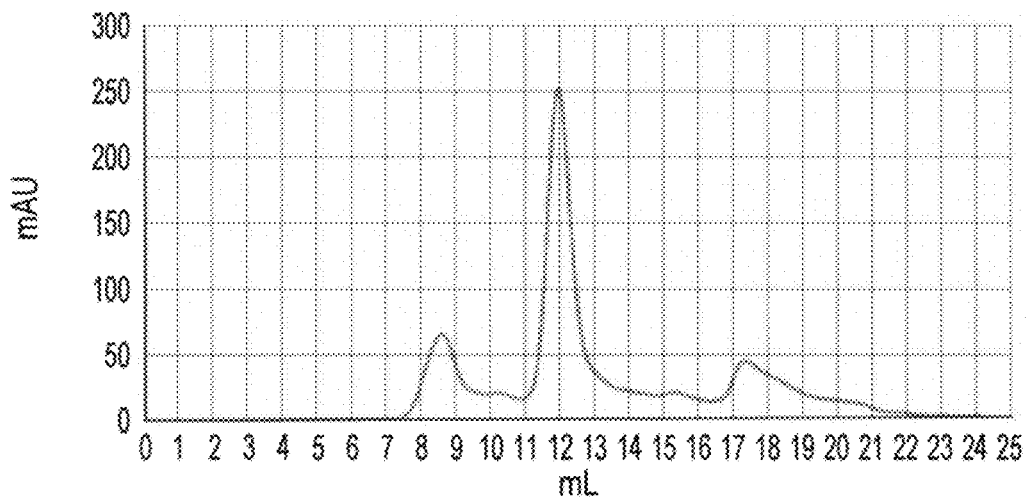
FIG. 15A is an elution curve when the ALP fusion antibody of Example 6 was gel-filtered.
Figure 15B:
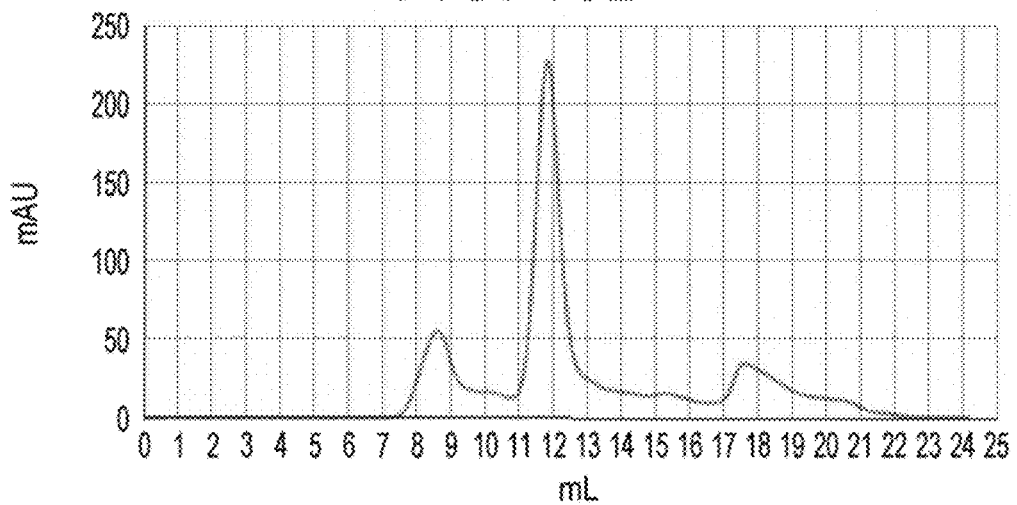
FIG. 15B is an elution curve when the ALP fusion antibody of Example 6 was gel-filtered.
Figure 15C:
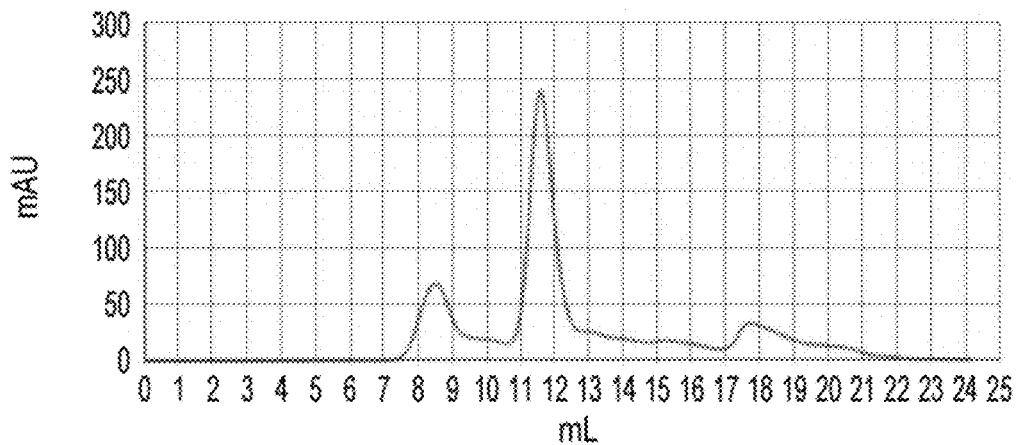
FIG. 15C is an elution curve when the ALP fusion antibody of Example 6 was gel-filtered.
Figure 16:
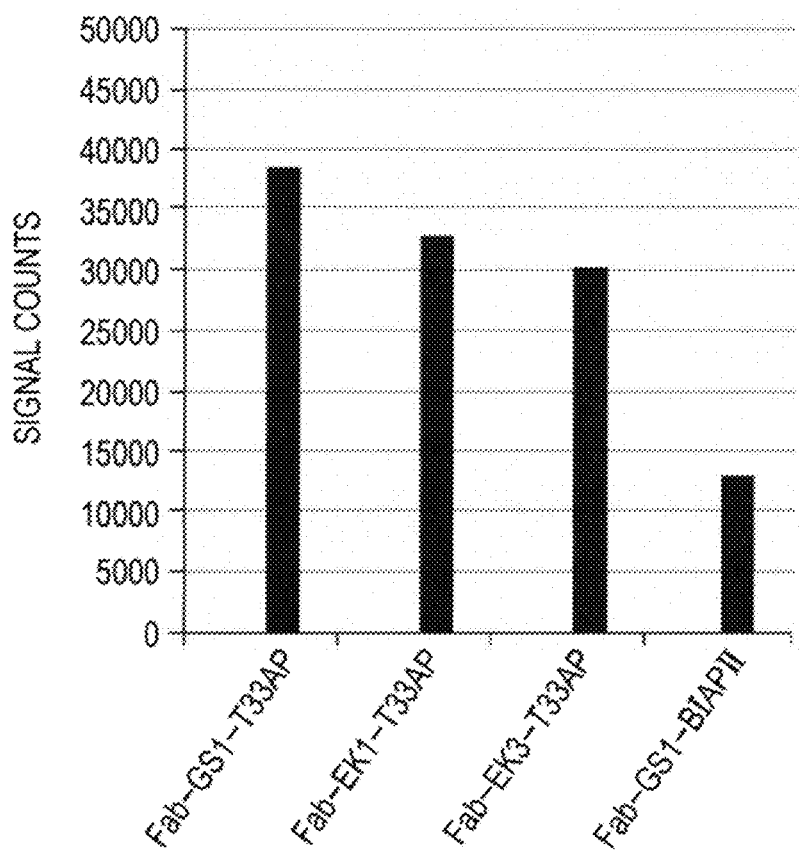
FIG. 16 is a graph showing ALP activities of the ALP fusion antibodies of Example 6.

As an ALP fusion antibody having a different ALP portion from that of the ALP fusion antibody of Example 1, a fusion protein in which Fab of a rabbit antibody and ALP derived from *Shewanella* bacteria were bound was prepared. This corresponds to the ALP fusion antibody having a structure shown in Antibody Example 1-1 above.
(1) Preparation of Expression Vector and Acquisition of Antibody
As an expression vector for the rabbit antibody, a plasmid DNA containing the gene of the rabbit anti-CD80 antibody of Example 1 was used. As a T3-3AP expression vector, a plasmid DNA containing a T3-3AP gene was acquired by outsourcing gene synthesis to GenScript, based on an amino acid sequence of ALP (T3-3AP) derived from the T3-3 strain described in U.S. Pat. No. 9,133,446. The amino acid sequence of T3-3AP and a base sequence encoding the same are shown in SEQ ID NOs: 3 and 4, respectively. An Fd-linker-T33AP expression vector was obtained in the same manner as in Example 1 except that the T3-3AP expression vector was used instead of the BIAPII expression vector. The peptide linkers were GS1, EK1 and EK3 linkers. This expression vector and the light chain expression vector obtained in Example 1 were transfected into Expi293F (trademark) cells to obtain an ALP fusion antibody.
(2) Examination of Homogeneity of Antibody Molecule and Measurement of ALP Activity
Homogeneity of molecules of each ALP fusion antibody were examined by gel filtration in the same manner as in Test Example 3. Elution curves are shown in FIGS. 15A to 15C. In gel filtration, each ALP-fused anti-CD80 antibody was eluted in a fraction of 11.5 mL to 12 mL. Using each ALP fusion antibody, ALP activities were measured in the same manner as in Test Example 2. For comparison, an ALP activity of the ALP fusion antibody (Fab-GS1-BIAPII) of Example 1 was also measured. The results are shown in FIG. 16. As shown in FIGS. 15A to 15C, the obtained ALP fusion antibodies were homogeneous molecular assemblies. As shown in FIG. 16, the ALP fusion antibodies having T3-3AP showed high ALP activity as well as the ALP fusion antibody having BIAPII.

(3) Immunoassay Using ALP Fusion Antibody (3.1) ELISA

Figure 17:
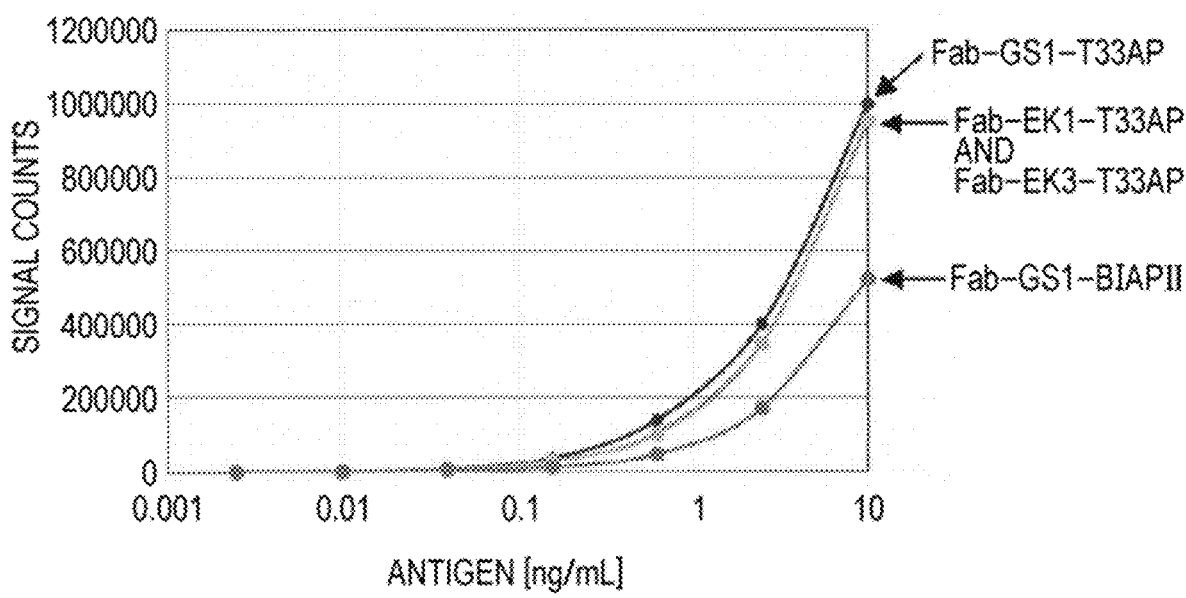
FIG. 17 is a graph showing results of measuring antigens by ELISA using the ALP fusion antibodies of Example 6.

ELISA was performed in the same manner as in Test Example 1 except that the ALP fusion antibodies obtained in (1) above were used as detection antibodies instead of the ALP fusion antibody of Example 1. For comparison, measurements using the ALP fusion antibody of Example 1 were also performed. The results are shown in FIG. 17. As shown in FIG. 17, the luminescence intensity of the ALP fusion antibody having T3-3AP increased according to antigen concentration, similar to the ALP fusion antibody having BIAPII. Therefore, the ALP fusion antibodies having T3-3AP all had antigen detection ability.

(3.2) Immunoassay Using Automatic Measuring Device

Figure 18A:
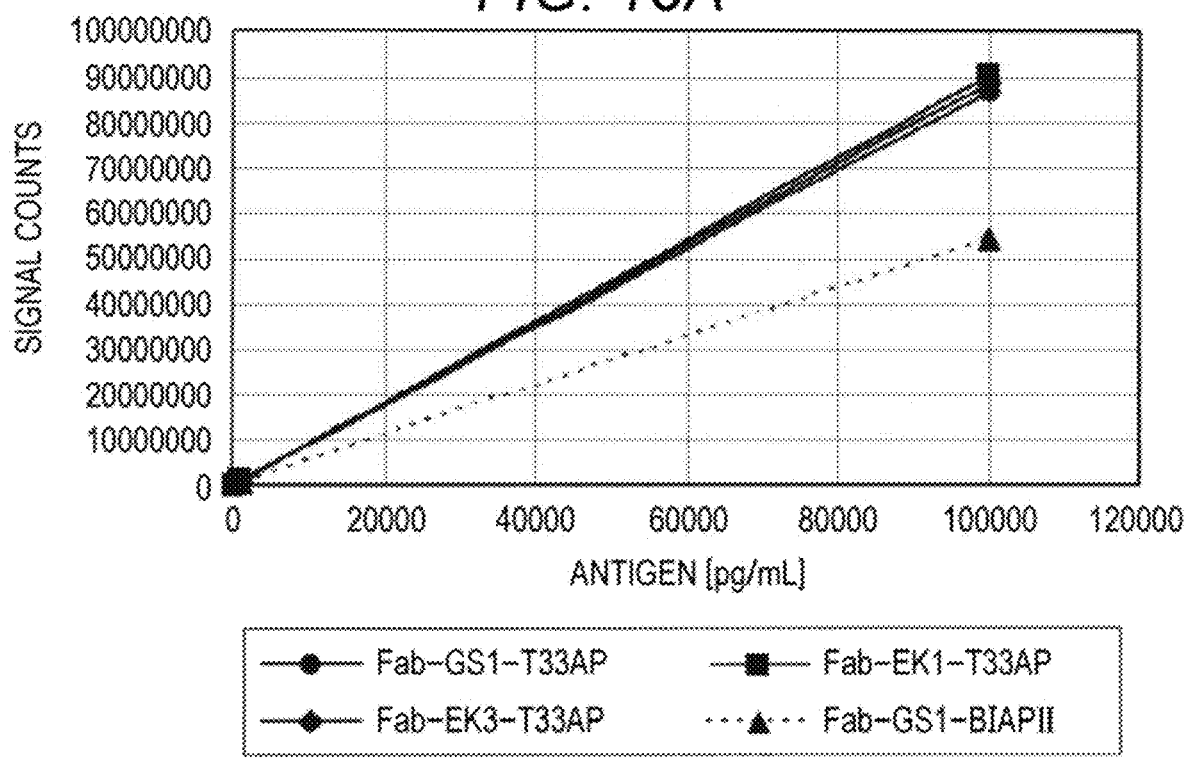
FIG. 18A is a graph showing luminescence intensities when immunoassayed with an automatic measuring device using the ALP fusion antibodies of Example 6.
Figure 18B:
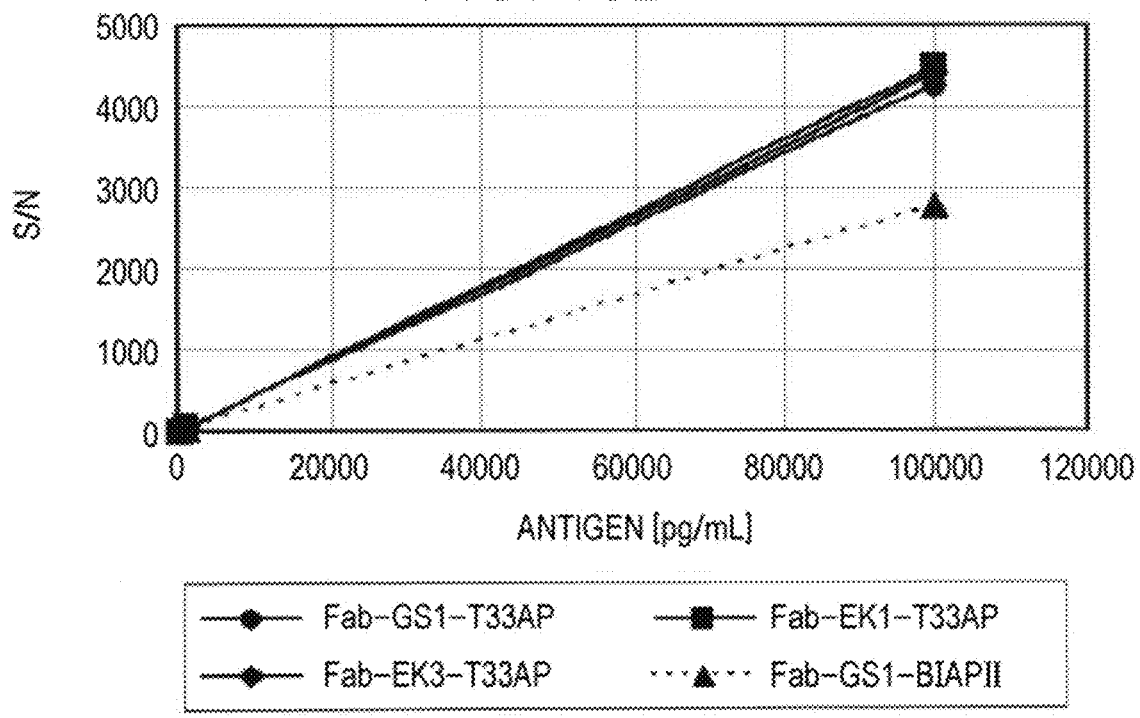
FIG. 18B is a graph showing SN ratios when immunoassayed with an automatic measuring device using the ALP fusion antibodies of Example 6.

Measurements were performed in the same manner as in Test Example 4 except that the R3 reagents containing the ALP fusion antibody obtained in (1) above were used instead of the ALP fusion antibody of Example 1. For comparison, measurements using the R3 reagents containing the ALP fusion antibody of Example 1 were also performed. The results are shown in FIGS. 18A and 18B. As shown in FIG. 18A, the luminescence intensity increased according to antigen concentration in the measurements using the R3 reagents containing the ALP fusion antibody having T3-3AP. As shown in FIG. 18B, the measurements using the R3 reagents showed high SN ratios.

[Reference Examples] Search for *Shewanella* Bacterium-Derived ALPs Other than T3-3AP In addition to T3-3AP, *Shewanella* bacterium-derived ALPs, which are useful for ALP fusion antibody, were searched as follows. Homology search program BLAST (NCBI) was used to search for *Shewanella*-derived ALPs having 69% or more homology with the amino acid sequence (excluding a signal sequence) of T3-3AP. As a result, 21 kinds of ALPs shown in Table 2 were selected as *Shewanella* bacterium-derived ALPs other than T3-3AP.

TABLE 2

| No. | Strain | Accession No. | Homology (%) |
|---|---|---|---|
| 1 | *Shewanella putrefaciens* CN-32 | WP_011788159.1 | 86.06 |
| 2 | *Shewanella xiamenensis* | WP_037428906.1 | 84.77 |
| 3 | *Shewanella oneidensis* | WP_011071122.1 | 83.78 |
| 4 | *Shewanella frigidimarina* | WP_011636029.1 | 71.57 |

TABLE 2-continued

| No. | Strain | Accession No. | Homology (%) |
|---|---|---|---|
| 5 | *Shewanella arctica* sp. | WP_123778009.1 | 71.57 |
| 6 | *Shewanella frigidimarina* | WP_082707432.1 | 71.08 |
| 7 | *Shewanella frigidimarina* NCIMB 400 | WP_102035892.1 | 71.57 |
| 8 | *Shewanella frigidimarina* | KVX00286.1 | 71.08 |
| 9 | *Shewanella livingstonensis* | WP_124729648.1 | 70.10 |
| 10 | *Shewanella* sp. R106 or M2 | WP_124014147.1 | 70.83 |
| 11 | *Shewanella* sp. ALD9 | WP_101086197.1 | 70.34 |
| 12 | *Shewanella frigidimarina* | WP_101032902.1 | 70.83 |
| 13 | *Shewanella colwelliana* | WP_037428448.1 | 73.40 |
| 14 | *Shewanella colwelliana* | WP_069670968.1 | 73.40 |
| 15 | *Shewanella* sp. CG18 | PIQ00530.1 | 70.10 |
| 16 | *Shewanella vesiculosa* | WP_124017315.1 | 69.85 |
| 17 | *Shewanella benthica* KT99 | EDQ02045.1 | 71.54 |
| 18 | *Shewanella benthica* | WP_040571562.1 | 71.54 |
| 19 | *Shewanella benthica* | SQH78322.1 | 70.79 |
| 20 | *Shewanella algidipiscicola* | WP_110455832.1 | 69.68 |
| 21 | *Shewanella benthica* | WP_112354238.1 | 70.79 |

The amino acid sequences of ALPs were clustered using sequence analysis software GENETYX (registered trademark) (GENETYX CORPORATION). Based on the clustering results, 6 types of ALPs (S-AP1, S-AP2, S-AP3, S-AP4, S-AP5 and S-AP6) shown in Table 3 were selected.

TABLE 3

| Code | No. | Strain | Accession No. |
|---|---|---|---|
| S-AP1 | 1 | *Shewanella putrefaciens* CN-32 | WP_011788159.1 |
| S-AP2 | 2 | *Shewanella xiamenensis* | WP_037428906.1 |
| S-AP3 | 4 | *Shewanella frigidimarina* | WP_011636029.1 |
| S-AP4 | 9 | *Shewanella livingstonensis* | WP_124729648.1 |
| S-AP5 | 12 | *Shewanella frigidimarina* | WP_101032902.1 |
| S-AP6 | 16 | *Shewanella vesiculosa* | WP_124017315.1 |

Figure 19:
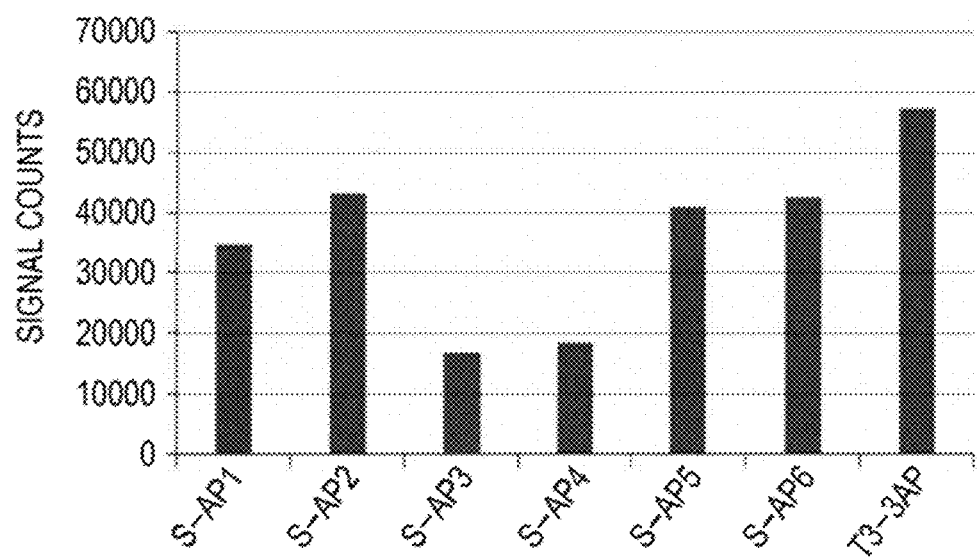
FIG. 19 is a graph showing ALP activities of *Shewanella* bacterium-derived ALP of Reference Examples.

Signal sequences of these ALPs were predicted by signal peptide prediction program SingalP-5.0 (DTU Health Tech). A plasmid DNA containing each ALP gene was acquired by outsourcing gene synthesis to GenScript, based on these amino acid sequences of ALPs. At the time of subcloning, a signal sequence of luciferase was inserted in place of the predicted signal sequence. The expression vectors of S-AP1, S-AP2, S-AP3, S-AP4, S-AP5 and S-AP6 were transfected into Expi293F (trademark) cells to recover ALPs and purified by gel filtration. Using purified ALPs, ALP activities were measured in the same manner as in Test Example 2. For comparison, an ALP activity of T3-3AP was also measured. The results are shown in FIG. 19. As shown in FIG. 19, it was shown that S-AP1, S-AP2, S-AP3, S-AP4, S-AP5 and S-AP6 are less active than T3-AP, but are promising candidates as ALPs used for ALP fusion antibodies.

What is claimed is:

1. A method for producing an alkaline phosphatase fusion antibody, comprising:
    culturing a cell comprising an expression vector comprising a gene encoding alkaline phosphatase from bovine small intestine or from *Shewanella* bacterium, and a gene encoding an antibody in a medium comprising a zinc ion, and
    acquiring an alkaline phosphatase fusion antibody expressed by the cell.

2. The production method according to claim 1, wherein the expression vector further comprises a gene encoding a peptide linker between the gene encoding alkaline phosphatase and the gene encoding an antibody, and
    in the alkaline phosphatase fusion antibody, the alkaline phosphatase and the antibody are bound via the peptide linker.

3. The production method according to claim 1, wherein
    in the expression vector, the gene encoding alkaline phosphatase and the gene encoding an antibody are directly linked, and
    in the alkaline phosphatase fusion antibody, the alkaline phosphatase and the antibody are directly bound.

4. The production method according to claim 1, wherein the alkaline phosphatase comprised in the alkaline phosphatase fusion antibody comprises two subunits; and
    wherein each subunit is a monomeric alkaline phosphatase protein.

5. The production method according to claim 4, wherein the antibody comprised in the alkaline phosphatase fusion antibody is bound to one or both of the two subunits.

6. The production method according to claim 1, wherein the antibody is at least one selected from a group consisting of IgG, reduced IgG, Fab, Fab', VHH, Fd, Fd', light chain, F(ab')2, Fv and scFv.

7. The production method according to claim 1, wherein the peptide linker comprises an amino acid sequence represented by any one of SEQ ID NOs: 5 to 10.

8. The production method according to claim 1, wherein zinc ion concentration in the medium is from 0.01 mM to 0.25 mM.

9. An alkaline phosphatase fusion antibody in which alkaline phosphatase from bovine small intestine or from *Shewanella* bacterium, and an antibody are bound directly or via a peptide linker;
    wherein the alkaline phosphatase comprised in the alkaline phosphatase fusion antibody comprises two subunits; and
    wherein each subunit is a monomeric alkaline phosphatase protein.

10. The alkaline phosphatase fusion antibody according to claim 9, wherein
    a C-terminal amino acid residue of the alkaline phosphatase and an N-terminal amino acid residue of the antibody are bound directly or via a peptide linker, or
    the N-terminal amino acid residue of the alkaline phosphatase and the C-terminal amino acid residue of the amino acid sequence of the antibody are bound directly or via a peptide linker.

11. The alkaline phosphatase fusion antibody according to claim 9, wherein the antibody comprised in the alkaline phosphatase fusion antibody is bound to one or both of the two subunits.

12. The alkaline phosphatase fusion antibody according to claim 9, wherein the antibody is at least one selected from a group consisting of IgG, reduced IgG, Fab, Fab', VHH, Fd, Fd', light chain, F(ab')2, Fv and scFv.

13. The alkaline phosphatase fusion antibody according to claim 9, wherein the peptide linker comprises an amino acid sequence represented by any one of SEQ ID NOs: 5 to 10.

14. A method for assaying a test substance, comprising:
    forming a complex on a solid phase, wherein the complex comprises: a capture substance that specifically binds to the test substance and immobilized on the solid phase; the test substance; and a detection antibody that specifically binds to the test substance, and wherein the detection antibody is an alkaline phosphatase fusion antibody in which alkaline phosphatase from bovine small intestine or from *Shewanella* bacterium, and an antibody are bound directly or via a peptide linker;
    reacting the complex on the solid phase with a substrate of the alkaline phosphatase; and
    detecting a signal generated in the reacting to detect the test substance,
    wherein the alkaline phosphatase comprised in the alkaline phosphatase fusion antibody comprises two subunits; and
    wherein each subunit is a monomeric alkaline phosphatase protein.

15. The method according to claim 14, wherein
    a C-terminal amino acid residue of the alkaline phosphatase and an N-terminal amino acid residue of the antibody are bound directly or via a peptide linker, or
    the N-terminal amino acid residue of the alkaline phosphatase and the C-terminal amino acid residue of the amino acid sequence of the antibody are bound directly or via a peptide linker.

16. The method according to claim 14, wherein the antibody comprised in the alkaline phosphatase fusion antibody is bound to one or both of the two subunits.

17. The method according to claim 14, wherein the antibody is at least one selected from a group consisting of IgG, reduced IgG, Fab, Fab', VHH, Fd, Fd', light chain, F(ab')2, Fv and scFv.

18. The method according to claim 14, wherein the peptide linker comprises an amino acid sequence represented by any one of SEQ ID NOs: 5 to 10.

* * * * *

SEQUENCE LISTING

<160> NUMBER OF SEQ ID NOS: 36

<210> SEQ ID NO 1
<211> LENGTH: 480
<212> TYPE: PRT
<213> ORGANISM: Bos taurus

<400> SEQUENCE: 1

Leu Ile Pro Ala Glu Glu Glu Asn Pro Ala Phe Trp Asn Arg Gln Ala
1               5                   10                  15

Ala Gln Ala Leu Asp Val Ala Lys Lys Leu Gln Pro Ile Gln Thr Ala
            20                  25                  30

```
Ala Lys Asn Val Ile Leu Phe Leu Gly Asp Gly Met Gly Val Pro Thr
         35                  40                  45
Val Thr Ala Thr Arg Ile Leu Lys Gly Gln Met Asn Gly Lys Leu Gly
 50                  55                  60
Pro Glu Thr Pro Leu Ala Met Asp Gln Phe Pro Tyr Val Ala Leu Ser
 65                  70                  75                  80
Lys Thr Tyr Asn Val Asp Arg Gln Val Pro Asp Ser Ala Gly Thr Ala
                 85                  90                  95
Thr Ala Tyr Leu Cys Gly Val Lys Gly Asn Tyr Arg Thr Ile Gly Val
                100                 105                 110
Ser Ala Ala Arg Tyr Asn Gln Cys Asn Thr Thr Arg Gly Asn Glu
            115                 120                 125
Val Thr Ser Val Ile Asn Arg Ala Lys Lys Ala Gly Lys Ala Val Gly
         130                 135                 140
Val Val Thr Thr Thr Arg Val Gln His Ala Ser Pro Ala Gly Ala Tyr
145                 150                 155                 160
Ala His Thr Val Asn Arg Asn Trp Tyr Ser Asp Ala Asp Leu Pro Ala
                165                 170                 175
Asp Ala Gln Lys Asn Gly Cys Gln Asp Ile Ala Ala Gln Leu Val Tyr
            180                 185                 190
Asn Met Asp Ile Asp Val Ile Leu Gly Gly Gly Arg Met Tyr Met Phe
        195                 200                 205
Pro Glu Gly Thr Pro Asp Pro Glu Tyr Pro Asp Ala Ser Val Asn
    210                 215                 220
Gly Val Arg Lys Asp Lys Gln Asn Leu Val Gln Glu Trp Gln Ala Lys
225                 230                 235                 240
His Gln Gly Ala Gln Tyr Val Trp Asn Arg Thr Ala Leu Leu Gln Ala
                245                 250                 255
Ala Asp Asp Ser Ser Val Thr His Leu Met Gly Leu Phe Glu Pro Ala
            260                 265                 270
Asp Met Lys Tyr Asn Val Gln Gln Asp His Thr Lys Asp Pro Thr Leu
        275                 280                 285
Ala Glu Met Thr Glu Ala Ala Leu Gln Val Leu Ser Arg Asn Pro Arg
    290                 295                 300
Gly Phe Tyr Leu Phe Val Glu Gly Gly Arg Ile Asp His Gly His His
305                 310                 315                 320
Asp Gly Lys Ala Tyr Met Ala Leu Thr Glu Ala Ile Met Phe Asp Asn
                325                 330                 335
Ala Ile Ala Lys Ala Asn Glu Leu Thr Ser Glu Leu Asp Thr Leu Ile
            340                 345                 350
Leu Val Thr Ala Asp His Ser His Val Phe Ser Phe Gly Gly Tyr Thr
        355                 360                 365
Leu Arg Gly Thr Ser Ile Phe Gly Leu Ala Pro Gly Lys Ala Leu Asp
    370                 375                 380
Ser Lys Ser Tyr Thr Ser Ile Leu Tyr Gly Asn Gly Pro Gly Tyr Ala
385                 390                 395                 400
Leu Gly Gly Gly Ser Arg Pro Asp Val Asn Gly Ser Thr Ser Glu Glu
                405                 410                 415
Pro Ser Tyr Arg Gln Gln Ala Ala Val Pro Leu Ala Ser Glu Thr His
            420                 425                 430
Gly Gly Glu Asp Val Ala Val Phe Ala Arg Gly Pro Gln Ala His Leu
        435                 440                 445
```

Val His Gly Val Gln Glu Glu Thr Phe Val Ala His Ile Met Ala Phe
450                 455                 460

Ala Gly Cys Val Glu Pro Tyr Thr Asp Cys Asn Leu Pro Ala Pro Ala
465                 470                 475                 480

<210> SEQ ID NO 2
<211> LENGTH: 1440
<212> TYPE: DNA
<213> ORGANISM: Bos taurus

<400> SEQUENCE: 2

```
ttaattccgg cagaagaaga aaacccggcg ttttggaacc gtcaggccgc acaggccctg      60
gatgtagcta aaaaacttca accgattcaa actgcagcca gaatgtgat cctgtttcta     120
ggggatggta tggggtccc gacagtgaca gctactcgta ttttgaaggg tcagatgaat     180
gggaagttgg gcccggaaac ccctcttgca atggatcaat tcccttatgt ggctctttca     240
aagacatata atgttgatcg tcaagtacca gatagcgcag gtactgccac cgcgtactta     300
tgcggggtga aggtaatta tcgtaccatt ggcgtatcgg cagctgctcg ctataaccag     360
tgtaatacca cccgtggaaa cgaagtgacc agcgtcatta accgcgcaaa gaaggcgggc     420
aaagcagtcg gcgtagtaac aacaactcgt gttcaacatg ctagcccggc tggcgcatac     480
gcacatacgg tcaatcgcaa ctggtattcg gatgccgacc ttccggctga tgctcaaaaa     540
aatggttgtc aagacatcgc ggcccaactt gtatacaata tggatatcga tgtcatcctt     600
ggcggcggcc gtatgtacat gtttcccgaa ggaaccccag atccggaata ccctgacgat     660
gcgtcggtga acggggtgcg taaagataaa cagaacttgg tccaagagtg gcaggccaaa     720
caccagggag ctcagtatgt ctggaatcga accgcgctgt tgcaggcagc agatgattcc     780
tcggttaccc acttaatggg acttttcgaa ccggccgata tgaaatacaa tgtccagcag     840
gaccacacaa aagaccctac cctggccgaa atgactgagg ccgcattaca agtcttaagc     900
cgtaaccca gagggttcta tctgttcgtt gagggcggcc gcatcgatca tgggcaccat     960
gatggcaaag cctatatggc ccttactgaa gccatcatgt tcgacaacgc gatagcgaag    1020
gcaaatgaat taacttctga actggatacc ctgatcttgg tgacagccga tcatagtcat    1080
gtattctcat ttgggggcta caccctgcgt ggtaccagta tctttggctt ggccccgggt    1140
aaggctctgg attccaagag ctatacctcc attctgtacg gtaacgggcc tgggtatgct    1200
cttgggggcg gttcgcgccc cgatgttaac ggttcaacgt ccgaagaacc ttcttatcgt    1260
cagcaggcag ccgtgccct cgcgagcgag acgcatggag gtgaggacgt ggcggtgttt    1320
gctcgcggtc cgcaggcgca tcttgtacac ggagtgcaag aggagacgtt tgtagctcat    1380
ataatggcgt tcgcaggttg cgtggagcct acacagatt gtaacttgcc tgcacctgcg    1440
```

<210> SEQ ID NO 3
<211> LENGTH: 443
<212> TYPE: PRT
<213> ORGANISM: Shewanella sp. T3-3

<400> SEQUENCE: 3

Met Ser Val Thr Lys Thr Ser Leu Leu Leu Thr Ile Gly Leu Val
1               5                   10                  15

Phe Ser Ala Ser Ser Lys Ala Ala Pro Glu Leu Glu Asn Gly Pro Met
                20                  25                  30

Lys Pro Pro Ser Lys Pro Lys Asn Ile Val Ile Met Val Gly Asp Gly
            35                  40                  45

Met Gly Pro Ser Tyr Thr Ser Ala Tyr Arg Tyr Phe Lys Asp Asn Pro
            50                  55                  60

Asp Thr Glu Glu Val Glu Gln Thr Val Phe Asp Arg Leu Leu Val Gly
 65                  70                  75                  80

Met Ala Ser Thr Tyr Pro Ala Ser Val Ser Gly Tyr Val Thr Asp Ser
                85                  90                  95

Ala Ala Ala Ala Thr Ala Leu Ala Thr Gly Val Lys Ser Tyr Asn Gly
                100                 105                 110

Ala Ile Ser Val Asp Thr Gln Lys Gln His Leu Pro Thr Met Leu Glu
            115                 120                 125

Lys Ala Lys Ala Leu Gly Leu Ser Thr Gly Val Ala Val Thr Ser Gln
130                 135                 140

Ile Asn His Ala Thr Pro Ala Ala Phe Leu Ala His Asn Glu Ser Arg
145                 150                 155                 160

Lys Asn Tyr Asp Ala Leu Ala Leu Ser Tyr Leu Asp Thr Asn Ala Asp
                165                 170                 175

Val Leu Leu Gly Gly Gln Lys Tyr Phe Ser Pro Glu Leu Leu Glu
                180                 185                 190

Lys Phe Thr Ala Lys Gly Tyr Gln His Ile Ser Arg Phe Glu Asp Leu
            195                 200                 205

Ala Thr Ile Thr Gln Pro Lys Val Ile Gly Leu Phe Ala Gln Val Gln
210                 215                 220

Leu Pro Trp Ala Leu Asp Glu Lys Asn Ala Asn Arg Leu Ser Thr Met
225                 230                 235                 240

Thr Gln Lys Ala Leu Asp Leu Leu Ser Gln Asn Glu Gln Gly Phe Val
                245                 250                 255

Leu Leu Val Glu Gly Ser Leu Ile Asp Trp Ala Gly His Ser Asn Asp
            260                 265                 270

Ile Ala Asn Thr Met Gly Glu Met Asp Glu Phe Ala Asn Ala Leu Glu
        275                 280                 285

Val Val Glu Gln Phe Val Arg Gln His Pro Asp Thr Leu Met Val Ala
    290                 295                 300

Thr Ala Asp His Asn Thr Gly Gly Leu Ser Ile Gly Ala Gly Gly Asp
305                 310                 315                 320

Tyr Arg Trp Asn Pro Glu Ile Leu Arg Asn Met Ser Ala Ser Thr Asp
                325                 330                 335

Thr Leu Ala Leu Ala Ala Leu Gly Gly Asp Gln Trp Gln Ala Asp Leu
            340                 345                 350

Ala Arg Gly Leu Gly Phe Glu Leu Asn Ala Asp Glu Val Thr Gln Leu
        355                 360                 365

Ser Thr Ala Arg Met Gln Gly Leu Glu Thr Met Thr Glu Ala Ile Arg
    370                 375                 380

Lys Ile Ile Asp Lys Arg Thr Gly Thr Gly Trp Thr Thr Ser Gly His
385                 390                 395                 400

Thr Gly Thr Asp Val Gln Val Phe Ala Ala Gly Pro Ala Ala Glu Leu
                405                 410                 415

Phe Asn Gly His Gln Asp Asn Thr Asp Ile Ala Asn Lys Ile Phe Thr
            420                 425                 430

Leu Leu Pro Lys Pro Lys Lys Ala Lys Thr Glu
            435                 440

<210> SEQ ID NO 4
<211> LENGTH: 1332
<212> TYPE: DNA

<213> ORGANISM: Shewanella sp. T3-3

<400> SEQUENCE: 4

```
atgagcgtca ccaaaacatc actcttattg ctgactatcg gattagtatt ttcagctagc    60
agcaaggccg cacccgagct tgaaaacggg cctatgaaac cgccatcaaa acctaaaaac   120
atcgttatta tggtgggtga cggcatgggc ccttcgtaca ccagcgccta ccgctatttc   180
aaagataatc ctgacaccga agaagtcgaa caaaccgtat tcgatagact cttagttggc   240
atggcaagta cgtatcctgc cagtgtcagc ggctatgtca cagattctgc tgcggcggca   300
actgcgctcg ccacaggcgt aaaatcttat aatggcgcta tttccgtcga tacccaaaag   360
caacacttac caaccatgct cgaaaaagcc aaagcattag ggttaagcac aggtgtggcg   420
gtaacatcac aaatcaacca tgccacgccc gcggcatttt tagcccacaa cgagagccgt   480
aaaaattacg atgctctggc gctcagttat ttagacacaa atgccgatgt acttttgggc   540
ggcggacaga agtatttctc gcctgaactg ctcgaaaaat tcaccgccaa aggttatcaa   600
cacattagcc gctttgaaga tttggccact ataacccaac ccaaagtcat tggcctgttt   660
gcacaggtgc aactgccttg ggcgctcgat gagaaaaatg caaatcgcct cagcactatg   720
actcaaaaag ccctcgattt actctcacaa atgagcaag gctttgtatt gttagtcgaa    780
ggcagcttga ttgactgggc cggacacagc aatgatatcg ccaacaccat gggcgaaatg   840
gatgaatttg ccaatgcact cgaagtggtt gagcagtttg tacgccaaca tccagacacc   900
ttaatggtag ccactgccga tcataatacc ggtggactct caattggtgc tggcggagat   960
tatcgctgga acccagagat tttacgcaat atgtctgcca gcacggacac gcttgcctta  1020
gccgcactcg gtggtgacca atggcaagcc gatctggccc gaggtttagg atttgagcta  1080
aacgccgatg aagtgactca attgagcaca gcccgaatgc aagtcttga aaccatgact   1140
gaagccattc gtaaaatcat cgacaagcgc accggcactg gctggacaac ctcaggccac  1200
actggcacag acgtacaagt atttgccgca ggccctgctg ccgagttatt taatggccac  1260
caagataata ccgacatagc caacaaaatt ttcactttat tgcctaaacc gaaaaaagcc  1320
aaaaccgaat aa                                                      1332
```

<210> SEQ ID NO 5
<211> LENGTH: 5
<212> TYPE: PRT
<213> ORGANISM: Artificial Sequence
<220> FEATURE:
<223> OTHER INFORMATION: Synthetic sequence, peptide linker

<400> SEQUENCE: 5

Gly Gly Gly Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic sequence, peptide linker

<400> SEQUENCE: 6

Gly Gly Gly Gly Ser Gly Gly Gly Gly Ser
1               5                   10

<210> SEQ ID NO 7
<211> LENGTH: 15

```
<212> TYPE: PRT
<213> ORGANISM: Artificial Sequence
<220> FEATURE:
<223> OTHER INFORMATION: Synthetic sequence, peptide linker

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 5
<212> TYPE: PRT
<213> ORGANISM: Artificial Sequence
<220> FEATURE:
<223> OTHER INFORMATION: Synthetic sequence, peptide linker

<400> SEQUENCE: 8

Glu Ala Ala Ala Lys
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic sequence, peptide linker

<400> SEQUENCE: 9

Glu Ala Ala Ala Lys Glu Ala Ala Ala Lys
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic sequence, peptide linker

<400> SEQUENCE: 10

Glu Ala Ala Ala Lys Glu Ala Ala Ala Lys Glu Ala Ala Ala Lys
1               5                   10                  15

<210> SEQ ID NO 11
<211> LENGTH: 220
<212> TYPE: PRT
<213> ORGANISM: Oryctolagus cuniculus

<400> SEQUENCE: 11

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Asn Ala
                20                  25                  30

Val Ser Trp Val Arg Gln Ala Pro Gly Glu Gly Leu Glu Trp Ile Gly
            35                  40                  45

Thr Ile Ser Ser Asn Asp Asn Thr Tyr Tyr Ala Thr Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Ile Tyr Tyr
                85                  90                  95

Tyr Gly Tyr Gly Tyr Val Phe Asn Leu Trp Gly Pro Gly Thr Leu Val
            100                 105                 110
```

Thr Val Ser Ser Gly Gln Pro Lys Ala Pro Ser Val Phe Pro Leu Ala
        115                 120                 125

Pro Cys Cys Gly Asp Thr Pro Ser Ser Thr Val Thr Leu Gly Cys Leu
    130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
                180                 185                 190

Pro Val Thr Cys Asn Val Ala His Pro Ala Thr Asn Thr Lys Val Asp
                195                 200                 205

Lys Thr Val Ala Pro Ser Thr Cys Ser Lys Pro Thr
    210                 215                 220

<210> SEQ ID NO 12
<211> LENGTH: 213
<212> TYPE: PRT
<213> ORGANISM: Oryctolagus cuniculus

<400> SEQUENCE: 12

Glu Leu Val Met Thr Gln Thr Pro Ala Ser Val Ser Glu Pro Val Gly
1               5                   10                  15

Gly Thr Val Thr Ile Asn Cys Gln Ala Ser Glu Asp Ile Tyr Ser Ser
                20                  25                  30

Leu Ala Trp Tyr Gln Gln Lys Pro Gly Gln Arg Pro Lys Leu Leu Met
            35                  40                  45

Tyr Tyr Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Leu Ser Ser Ser
                85                  90                  95

Ser Arg Tyr Gly Asn Ala Phe Gly Gly Gly Thr Glu Val Val Val Lys
                100                 105                 110

Gly Asp Pro Val Ala Pro Thr Val Leu Ile Phe Pro Pro Ala Ala Asp
                115                 120                 125

Gln Val Ala Thr Gly Thr Val Thr Ile Val Cys Val Ala Asn Lys Tyr
                130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
                180                 185                 190

His Lys Glu Tyr Thr Cys Lys Val Thr Gln Gly Thr Thr Ser Val Val
                195                 200                 205

Gln Ser Phe Ile Gly
    210

<210> SEQ ID NO 13
<211> LENGTH: 660
<212> TYPE: DNA
<213> ORGANISM: Oryctolagus cuniculus

<400> SEQUENCE: 13

```
cagtcggtgg aggagtccgg gggtcgcctg gtcacgcctg ggacacccct gacactcacc      60
tgcacagcct ctggattctc cctcagtaat aatgcagtga gctgggtccg ccaggctcca     120
ggggaggggc tggaatggat cggaaccatt agtagtaatg ataacacata ttatgcgacc     180
tgggcgaaag gccgattcac catctccaaa acctcgacca cggtggatct gaaaatcacc     240
agtccgacaa ccgaggacac ggccacctat ttctgtgcca tctattatta tggttatggt     300
tatgttttta acttgtgggg cccaggcact ctggtcaccg tctcctcagg caacctaag      360
gctccatcag tcttcccact ggcccccctgc tgcggggaca cacccagctc cacggtgacc    420
ctgggctgcc tggtcaaagg ctacctcccg gagccagtga ccgtgacctg gaactcgggc    480
accctcacca atggggtacg caccttcccg tccgtccggc agtcctcagg cctctactcg    540
ctgagcagcg tggtgagcgt gacctcaagc agccagcccg tcacctgcaa cgtggcccac    600
ccagccacca acaccaaagt ggacaagacc gttgcgccct cgacatgcag caagcccacg    660
```

<210> SEQ ID NO 14
<211> LENGTH: 650
<212> TYPE: DNA
<213> ORGANISM: Oryctolagus cuniculus

<400> SEQUENCE: 14

```
gctatcgcag cgagctcgtg atgacccaga ctccagcctc cgtgtctgag cctgtgggag      60
gcacagtcac catcaattgc caggccagtg aggatattta cagctctttt gcctggtatc     120
agcagaaacc agggcagcgt cccaagctcc ttatgtatta tgcatccact ctggcatctg     180
gggtcccatc gcggttcaaa ggcagtggat ctgggacaga gttcactctc accatcagcg     240
acctggagtg tgccgatgct gccacttact actgtcaaag ctattatctt agtagtagta     300
gtaggtatgg taatgcgttc ggcggaggga ccgaggtggt ggtcaaaggt gatccagttg     360
cacctactgt cctcatcttc ccaccagctg ctgatcaggt ggcaactgga acagtcacca     420
tcgtgtgtgt ggcgaataaa tactttcccg atgtcaccgt cacctgggag gtggatggca     480
ccacccaaac aactggcatc gagaacagta aaacaccgca gaattctgca gattgtacct     540
acaacctcag cagcactctg acactgacca gcacacagta caacagccac aaagagtaca     600
cctgcaaggt gacccagggc acgacctcag tcgtccagag cttcataggg                650
```

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence, primer

<400> SEQUENCE: 15

```
tgataaaagg gttcgatccc tacc                                             24
```

<210> SEQ ID NO 16
<211> LENGTH: 25
<212> TYPE: DNA
<213> ORGANISM: Artificial Sequence
<220> FEATURE:
<223> OTHER INFORMATION: Synthetic sequence, primer

<400> SEQUENCE: 16

```
gcagtgcacg gtggcgcagt acacc                                            25
```

<210> SEQ ID NO 17
<211> LENGTH: 40
<212> TYPE: DNA
<213> ORGANISM: Artificial Sequence
<220> FEATURE:
<223> OTHER INFORMATION: Synthetic sequence, primer

<400> SEQUENCE: 17
gccaccgtgc actgcttaat tccggcagaa gaagaaaacc          40

<210> SEQ ID NO 18
<211> LENGTH: 39
<212> TYPE: DNA
<213> ORGANISM: Artificial Sequence
<220> FEATURE:
<223> OTHER INFORMATION: Synthetic sequence, primer

<400> SEQUENCE: 18
cgaacccttt tatcacgcag gtgcaggcaa gttacaatc           39

<210> SEQ ID NO 19
<211> LENGTH: 40
<212> TYPE: DNA
<213> ORGANISM: Artificial Sequence
<220> FEATURE:
<223> OTHER INFORMATION: Synthetic sequence, primer

<400> SEQUENCE: 19
ggtggcggtg gatccttaat tccggcagaa gaagaaaacc          40

<210> SEQ ID NO 20
<211> LENGTH: 48
<212> TYPE: DNA
<213> ORGANISM: Artificial Sequence
<220> FEATURE:
<223> OTHER INFORMATION: Synthetic sequence, primer

<400> SEQUENCE: 20
gtggatccgg aggggcgga agtttaattc cggcagaaga agaaaacc  48

<210> SEQ ID NO 21
<211> LENGTH: 55
<212> TYPE: DNA
<213> ORGANISM: Artificial Sequence
<220> FEATURE:
<223> OTHER INFORMATION: Synthetic sequence, primer

<400> SEQUENCE: 21 ggaggggggcg gaagtggcgg gggaggttca ttaattccgg cagaagaaga aaacc    55

<210> SEQ ID NO 22
<211> LENGTH: 40
<212> TYPE: DNA
<213> ORGANISM: Artificial Sequence
<220> FEATURE:
<223> OTHER INFORMATION: Synthetic sequence, primer

<400> SEQUENCE: 22
gaagccgctg ctaagttaat tccggcagaa gaagaaaacc          40

<210> SEQ ID NO 23
<211> LENGTH: 48
<212> TYPE: DNA
<213> ORGANISM: Artificial Sequence
<220> FEATURE:
<223> OTHER INFORMATION: Synthetic sequence, primer

<400> SEQUENCE: 23
ctgctaagga ggcagccgcg aaattaattc cggcagaaga agaaaacc                48

<210> SEQ ID NO 24
<211> LENGTH: 55
<212> TYPE: DNA
<213> ORGANISM: Artificial Sequence
<220> FEATURE:
<223> OTHER INFORMATION: Synthetic sequence, primer

<400> SEQUENCE: 24
gaggcagccg cgaaagaagc agcggctaaa ttaattccgg cagaagaaga aaacc         55

<210> SEQ ID NO 25
<211> LENGTH: 25
<212> TYPE: DNA
<213> ORGANISM: Artificial Sequence
<220> FEATURE:
<223> OTHER INFORMATION: Synthetic sequence, primer

<400> SEQUENCE: 25
gcagtgcacg gtggcgcagt acacc                                          25

<210> SEQ ID NO 26
<211> LENGTH: 35
<212> TYPE: DNA
<213> ORGANISM: Artificial Sequence
<220> FEATURE:
<223> OTHER INFORMATION: Synthetic sequence, primer

<400> SEQUENCE: 26
gccaccgtgc actgccagtc ggtggaggag tccgg                               35

<210> SEQ ID NO 27
<211> LENGTH: 39
<212> TYPE: DNA
<213> ORGANISM: Artificial Sequence
<220> FEATURE:
<223> OTHER INFORMATION: Synthetic sequence, primer

<400> SEQUENCE: 27
ggatccaccg ccacccgtgg gcttgctgca tgtcgaggg                           39

<210> SEQ ID NO 28
<211> LENGTH: 47
<212> TYPE: DNA
<213> ORGANISM: Artificial Sequence
<220> FEATURE:
<223> OTHER INFORMATION: Synthetic sequence, primer

<400> SEQUENCE: 28 cccctccgg atccaccgcc acccgtgggc ttgctgcatg tcgaggg                   47

<210> SEQ ID NO 29
<211> LENGTH: 54
<212> TYPE: DNA
<213> ORGANISM: Artificial Sequence
<220> FEATURE:
<223> OTHER INFORMATION: Synthetic sequence, primer

<400> SEQUENCE: 29
acttccgccc cctccggatc caccgccacc cgtgggcttg ctgcatgtcg aggg          54

<210> SEQ ID NO 30
<211> LENGTH: 39
<212> TYPE: DNA
<213> ORGANISM: Artificial Sequence
<220> FEATURE:
<223> OTHER INFORMATION: Synthetic sequence, primer

<400> SEQUENCE: 30
cttagcagcg gcttccgtgg gcttgctgca tgtcgaggg                      39

<210> SEQ ID NO 31
<211> LENGTH: 47
<212> TYPE: DNA
<213> ORGANISM: Artificial Sequence
<220> FEATURE:
<223> OTHER INFORMATION: Synthetic sequence, primer

<400> SEQUENCE: 31
gctgcctcct tagcagcggc ttccgtgggc ttgctgcatg tcgaggg              47

<210> SEQ ID NO 32
<211> LENGTH: 54
<212> TYPE: DNA
<213> ORGANISM: Artificial Sequence
<220> FEATURE:
<223> OTHER INFORMATION: Synthetic sequence, primer

<400> SEQUENCE: 32
tttcgcggct gcctccttag cagcggcttc cgtgggcttg ctgcatgtcg aggg      54

<210> SEQ ID NO 33
<211> LENGTH: 24
<212> TYPE: DNA
<213> ORGANISM: Artificial Sequence
<220> FEATURE:
<223> OTHER INFORMATION: Synthetic sequence, primer

<400> SEQUENCE: 33
taatctagat aattaaaggg ttcg                                       24

<210> SEQ ID NO 34
<211> LENGTH: 25
<212> TYPE: DNA
<213> ORGANISM: Artificial Sequence
<220> FEATURE:
<223> OTHER INFORMATION: Synthetic sequence, primer

<400> SEQUENCE: 34
gctgcgatag cccggaaaca gtacc                                      25

<210> SEQ ID NO 35
<211> LENGTH: 35
<212> TYPE: DNA
<213> ORGANISM: Artificial Sequence
<220> FEATURE:
<223> OTHER INFORMATION: Synthetic sequence, primer

<400> SEQUENCE: 35
ccgggctatc gcagcgagct cgtgatgacc cagac                           35

<210> SEQ ID NO 36
<211> LENGTH: 38
<212> TYPE: DNA
<213> ORGANISM: Artificial Sequence
<220> FEATURE:

```
<223> OTHER INFORMATION: Synthetic sequence, primer

<400> SEQUENCE: 36
taattatcta gattatcaac agtcacccct attgaagc                                    38
```